US010947483B2

(12) United States Patent
Smets et al.

(10) Patent No.: US 10,947,483 B2
(45) Date of Patent: *Mar. 16, 2021

(54) ENCAPSULATES

(71) Applicant: Procter & Gamble International Operations SA, Geneva (CH)

(72) Inventors: Johan Smets, Lubbeek (BE); Susana Fernandez Prieto, Benicarlo (ES); Raul Rodrigo Gomez, Golmayo (ES); Albert Gasull Morales, El morell (ES); Jennifer Efua Kwansima Quansah, Accra (GH)

(73) Assignee: Procter & Gamble International Operations SA, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/679,465

(22) Filed: Nov. 11, 2019

(65) Prior Publication Data

US 2020/0071639 A1 Mar. 5, 2020

Related U.S. Application Data

(63) Continuation of application No. 15/402,425, filed on Jan. 10, 2017, now Pat. No. 10,604,728, which is a continuation of application No. 14/274,789, filed on May 12, 2014, now abandoned.

(30) Foreign Application Priority Data

May 20, 2013 (EP) .................... 13168427

(51) Int. Cl.
| | |
|---|---|
| C11D 3/50 | (2006.01) |
| C11D 3/37 | (2006.01) |
| B01J 13/04 | (2006.01) |
| C11D 17/00 | (2006.01) |
| C11D 3/386 | (2006.01) |
| C11D 3/40 | (2006.01) |
| C11D 3/42 | (2006.01) |
| C11D 11/02 | (2006.01) |
| A61K 8/66 | (2006.01) |
| A61K 8/11 | (2006.01) |
| A61Q 13/00 | (2006.01) |
| A61K 8/81 | (2006.01) |
| A61K 8/891 | (2006.01) |
| C09B 67/02 | (2006.01) |
| C09B 23/14 | (2006.01) |

(52) U.S. Cl.
CPC ............ *C11D 3/505* (2013.01); *A61K 8/11* (2013.01); *A61K 8/66* (2013.01); *A61K 8/8129* (2013.01); *A61K 8/8152* (2013.01); *A61K 8/891* (2013.01); *A61Q 13/00* (2013.01); *B01J 13/043* (2013.01); *C09B 23/148* (2013.01); *C09B 67/0097* (2013.01); *C11D 3/373* (2013.01); *C11D 3/3734* (2013.01); *C11D 3/3738* (2013.01); *C11D 3/3742* (2013.01); *C11D 3/3753* (2013.01); *C11D 3/3757* (2013.01); *C11D 3/38672* (2013.01); *C11D 3/40* (2013.01); *C11D 3/42* (2013.01); *C11D 11/02* (2013.01); *C11D 17/0039* (2013.01); *C12Y 302/01* (2013.01); *C12Y 302/01004* (2013.01); *C12Y 304/00* (2013.01); *A61K 2800/412* (2013.01); *A61K 2800/43* (2013.01); *A61K 2800/434* (2013.01); *A61K 2800/56* (2013.01); *A61K 2800/624* (2013.01)

(58) Field of Classification Search
CPC .................................. C11D 3/505; C11D 3/42
See application file for complete search history.

(56) References Cited

U.S. PATENT DOCUMENTS

| | | | | |
|---|---|---|---|---|
| 4,145,184 A * | 3/1979 | Brain | ...................... | C11D 3/505 8/137 |
| 6,413,920 B1 * | 7/2002 | Bettiol | ................. | C11D 3/2093 510/101 |
| 6,451,751 B1 * | 9/2002 | Busch | ................... | C11D 1/667 510/101 |
| 6,790,815 B1 * | 9/2004 | Bettiol | ................... | C11D 3/001 510/101 |
| 6,849,591 B1 * | 2/2005 | Boeckh | ................ | C11D 3/3761 510/101 |
| 7,285,523 B1 * | 10/2007 | Seydel | ............... | C11D 3/38672 510/441 |
| 2003/0211963 A1 * | 11/2003 | Bettiol | ................... | C11D 3/227 510/499 |

(Continued)

OTHER PUBLICATIONS

Rodrigo Bocanegra, et al. "Monodisperse Structured Multi-Vesicle Microencapsulation Using Flow-Focusing and Controlled Disturbance", Journal of Microencapsulation, vol. 22, No. 7 Nov. 2005; pp. 745-759; XP055061789.

(Continued)

*Primary Examiner* — Mark Eashoo
*Assistant Examiner* — M. Reza-Asdjodi
(74) *Attorney, Agent, or Firm* — James E Oehlenschlager

(57) ABSTRACT

The present application relates processes that can be used to produce encapsulated benefit agents comprising a core and a shell that encapsulates said core, encapsulated benefit agents produced by such process and products comprising such encapsulated benefit agents as well as methods of making and using such products. Such process can be used to produce particles that offer the desired protection and release benefits when used in a variety of products.

13 Claims, No Drawings

(56) References Cited

U.S. PATENT DOCUMENTS

| | | | | |
|---|---|---|---|---|
| 2003/0228992 | A1* | 12/2003 | Smets | C11D 17/065 510/267 |
| 2004/0018955 | A1* | 1/2004 | Wevers | C11D 3/3738 512/27 |
| 2004/0053808 | A1* | 3/2004 | Raehse | C11D 17/049 510/447 |
| 2004/0259749 | A1* | 12/2004 | Braeckman | C11D 17/0091 510/220 |
| 2007/0202063 | A1* | 8/2007 | Dihora | B01J 13/02 424/70.1 |
| 2008/0227676 | A1* | 9/2008 | Bettiol | C11D 3/37 510/106 |
| 2010/0330290 | A1* | 12/2010 | Dobler | B05C 5/005 427/420 |
| 2011/0021408 | A1* | 1/2011 | Meek | C11D 3/0036 510/321 |
| 2011/0097369 | A1* | 4/2011 | Sunder | C11D 17/0039 424/401 |
| 2011/0245134 | A1* | 10/2011 | Smets | C11D 3/39 510/375 |
| 2011/0245136 | A1* | 10/2011 | Smets | C11D 3/38672 510/513 |
| 2011/0268778 | A1 | 11/2011 | Dihora et al. | |
| 2011/0269657 | A1* | 11/2011 | Dihora | C11D 3/001 510/119 |
| 2014/0338134 | A1* | 11/2014 | Fernandez Prieto | C11D 17/0039 8/137 |
| 2014/0342972 | A1* | 11/2014 | Smets | A61K 8/8129 510/438 |
| 2017/0130172 | A1 | 5/2017 | Morales et al. | |
| 2020/0071639 | A1* | 3/2020 | Smets | C12Y 302/1004 |

OTHER PUBLICATIONS

PCT Search Report dated Aug. 27, 2014: PCT/US2014/038857; 11 Pages.
All Office Actions, U.S. Appl. No. 15/402,425.

* cited by examiner

ENCAPSULATES

FIELD OF INVENTION

The present application relates processes that can be used to produce encapsulated benefit agents comprising a core and a shell that encapsulates said core, encapsulated benefit agents produced by such process and products comprising such encapsulated benefit agents as well as methods of making and using such products.

BACKGROUND OF THE INVENTION

Products, for example, consumer products may comprise one or more benefit agents that can provide a desired benefit to such product and/or a situs that is contacted with such a product—for example hueing and/or suds suppression. Unfortunately, in certain products, for example, fluid products, benefit agents may be degraded by or degrade components of such products before such product is used. Thus, a protection system that protects the components of a product from a benefit agent and provides the desired level of benefit agent at the desired time was needed. Efforts have been made in this area but typically fail to provide the required level of protection and/or benefit agent release profile. In addition, many materials, such as hueing dyes, are liquid materials that are dispersible or soluble in aqueous and organic environments. Thus, such materials cannot be encapsulated by traditional methods. Thus, the need for encapsulated benefit agents that do not damage such products during product storage, yet deliver the desired release profile remains.

Previous attempts to produce encapsulated benefit agents using flow focusing have been made. Such attempts met with limited success as the resulting encapsulated benefit agents were not symmetric, mono-disperse and/or did not have a uniform core shell architecture. Applicants recognized that the source of such problems was unfavorable momentum and mass transfer through the nozzle. Applicants recognized that the judicious selection of fluid viscosity and/or concentration, nozzle flow rate and nozzle characteristics could minimize such problems. Thus, Applicants disclose a process that results in particles that offer the desired protection and release benefits.

SUMMARY OF THE INVENTION

The present application relates processes that can be used to produce encapsulated benefit agents comprising a core and a shell that encapsulates said core, encapsulated benefit agents produced by such process and products comprising such encapsulated benefit agents as well as methods of making and using such products. Such process can be used to produce particles that offer the desired protection and release benefits when used in a variety of products.

DETAILED DESCRIPTION OF THE INVENTION

Definitions

As used herein "consumer product" means baby care, beauty care, fabric & home care, family care, feminine care, health care, or devices generally intended to be used in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshing), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/ or freshing), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshing that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which are applicable may be in standard, concentrated or even highly concentrated form even to the extent that such products may in certain aspect be non-aqueous.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "situs" includes paper products, fabrics, garments, hard surfaces, hair and skin.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Encapsulated Benefit Agent

In one aspect, a population of encapsulated benefit agents having a population diameter coefficient of variation from about 6% to about 50%, from about 8% to about 35% or even from about 12% to about 25%, said population of encapsulated benefit agents may comprise encapsulated benefit agents having a mean diameter of from about 3 micrometers to about 300 micrometers, from about 5 micrometers to about 240 micrometers or even from about 10 micrometers to about 120 micrometers, said encapsulated benefit agent may comprise a core and a shell that encapsulates said core, said shell comprising a polymer, in one aspect a film forming polymer, said shell may have a thickness of from about 0.5 micrometers to about 15 micrometers, from about 1 micrometer to about 8 micrometers or even from about 1.5 micrometers to about 6 micrometers and a shell thickness coefficient of variation from about 2% to about 30%, from about 4% to about 25% or even from about 6% to about 20% is disclosed.

In one aspect, said core may comprise a material selected from the group consisting of a perfume, a hueing agent, a brightener, a silicone, an enzyme and mixtures thereof.

In one aspect,
a) said perfume may comprise a material selected from the group consisting of prop-2-enyl 3-cyclohexylpropanoate, (4aR,5R,7aS,9R)-octahydro-2,2,5,8,8,9a-hexamethyl-4h-4a,9-methanoazuleno(5,6-d)-1,3-dioxole, (3aR,5aS,9aS,9bR)-3a,6,6,9a-tetramethyl-2,4,5,5a,7,8,9,9b-octahydro-1H-benzo[e][1]benzofuran, 4-methoxybenzaldehyde, benzyl 2-hydroxybenzoate, 2-methoxynaphthalene, 3-(4-tert-butylphenyl)propanal, 3a,6,6,9a-tetramethyl-2,4,5,5a,7,8,9,9b-octahydro-1H-benzo[e][1]benzofuran, 3,7-dimethyloct-6-en-1-ol, 3,7-dimethyloct-6-enenitrile, 3-(4-tert-butylphenyl)butanal, 3-(4-propan-2-ylphenyl)butanal, (E)-1-(2,6,6-trimethyl-1-cyclohexa-1,3-dienyl)but-2-en-1-one, decanal, (E)-1-(2,6,6-trimethyl-1-cyclohex-3-enyl)but-2-en-1-one, (5E)-3-methylcyclopentadec-5-en-1-one, 2,6-dimethyloct-7-en-2-ol, ethyl 2-methylpentanoate, ethyl 2-methylbutanoate, 1,3,3-trimethyl-2-oxabicyclo[2,2,2]octane, 2-methoxy-4-prop-2-enylphenol, 3a,4,5,6,7,7a-hexahydro-4,7-methano-1H-indenyl acetate, 3-(3-propan-2-ylphenyl)butanal, a,4,5,6,7,7a-hexahydro-1H-4,7-methanoinden-1-yl propanoate, (2E)-3,7-dimethylocta-2,6-dien-1-ol, (12E)-1-oxacyclohexadec-12-en-2-one, [2-[1-(3,3-dimethylcyclohexyl)ethoxy]-2-methylpropyl]propanoate, hexyl acetate, 2-(phenylmethylidene)octanal, hexyl 2-hydroxybenzoate, (E)-4-(2,6,6-trimethyl-1-cyclohex-2-enyl)but-3-en-2-one, (E)-4-(2,6,6-trimethyl-1-cyclohexenyl)but-3-en-2-one, (E)-3-methyl-4-(2,6,6-trimethyl-1-cyclohex-2-enyl)but-3-en-2-one, 1-(2,3,8,8-tetramethyl-1,3,4,5,6,7-hexahydronaphthalen-2-yl)ethanone, propan-2-yl 2-methylbutanoate, (1R,2S,5R)-5-methyl-2-propan-2-ylcyclohexan-1-ol, (E)-2-ethyl-4-(2,2,3-trimethyl-1-cyclopent-3-enyl)but-2-en-1-ol, 2,4-dimethylcyclohex-3-ene-1-carbaldehyde, 3,7-dimethylocta-1,6-dien-3-ol, 3,7-dimethylocta-1,6-dien-3-yl acetate, 1-((3R,3aS,7R,8aS)-2,3,4,7,8,8a-hexahydro-3,6,8,8-tetramethyl-1H-3a,7-methanoazulen-5-yl)-ethanone, methyl 3-oxo-2-pentylcyclopentaneacetate, 2-methylundecanal, 2-[2-(4-methyl-1-cyclohex-3-enyl)propyl]cyclopentan-1-one, 1-(5,5-dimethyl-1-cyclohexenyl)pent-4-en-1-one, 2-cyclohexylidene-2-phenylacetonitrile, 2-phenylethanol, 3,7-dimethyloctan-3-ol, 5-heptyloxolan-2-one, (2-tert-butylcyclohexyl) acetate, (E)-4-methyldec-3-en-5-ol, (4-tert-butylcyclohexyl) acetate, decahydro-2,2,6,6,7,8,8-heptamethyl-2H-indeno(4,5-b)furan, 17-oxacycloheptadec-6-en-1-one, pentyl 2-hydroxybenzoate, benzyl acetate, 4-phenylbutan-2-one, 2-methoxynaphthalene, 1,7,7-trimethylbicyclo[2.2.1]heptan-2-one, 1,1,2,3,3-pentamethyl-2,5,6,7-tetrahydro-inden-4-one, 1H-3a,7-Methanoazulene, octahydro-6-methoxy-3,6,8,8-tetramethyl, [(Z)-hex-3-enyl] acetate, [(Z)-hex-3-enyl] 2-hydroxybenzoate, (9Z)-cycloheptadec-9-en-1-one, chromen-2-one, cyclohexyl 2-hydroxybenzoate, ethyl 3-methyl-3-phenyloxirane-2-carboxylate, 3-ethoxy-4-hydroxybenzaldehyde, 1,4-dioxacycloheptadecane-5,17-dione, 16-oxacyclohexadecan-1-one, diethyl cyclohexane-1,4-dicarboxylate, 1-(5,5-dimethyl-1-cyclohexenyl)pent-4-en-1-one, [(2E)-3,7-dimethylocta-2,6-dienyl] acetate, 3-(1,3-benzodioxol-5-yl)-2-methylpropanal, 1,3-benzodioxole-5-carbaldehyde, 6-(pent-3-en-1-yl)tetrahydro-2H-pyran-2-one, [(1R,2S)-1-methyl-2-[[(1R,3S,5S)-1,2,2-trimethyl-3-bicyclo[3.1.0]hexanyl]methyl]cyclopropyl]methanol, (Z)-3,4,5,6,6-pentamethyl-hept-3-en-2-one, dodecanal, 3,7- dimethylnona-2,6-dienenitrile, (2S)-2-aminopentanedioic acid, methyl 2,4-dihydroxy-3,6-dimethylbenzoate, 2,6-dimethyloct-7-en-2-ol, 4-(4-hydroxy-4-methylpentyl)cyclohex-3-ene-1-carbaldehyde, 1-naphthalen-2-ylethanone, 4-methyl-2-(2-methylprop-1-enyl)oxane, 1H-Indene-ar-propanal, 2,3-dihydro-1,1-dimethyl-(9CI), nonanal, octanal, 2-phenylethyl 2-phenylacetate, 3-methyl-5-phenylpentan-1-ol, 4-methyl-2-(2-methylpropyl)oxan-4-ol, 1-oxacycloheptadecan-2-one, 1-(spiro[4.5]dec-7-en-7-yl)pent-4-en-1-one, 2-(4-methyl-1-cyclohex-3-enyl)propan-2-ol, 1-methyl-4-propan-2-ylidenecyclohexene, (4-methyl-1-propan-2-yl-1-cyclohex-2-enyl) acetate, 1,2-dimethylcyclohex-3-ene-1-carbaldehyde, undec-10-enal, [(4Z)-1-cyclooct-4-enyl] methyl carbonate, 8-methyl-1,5-benzodioxepin-3-one, nona-2,6-dienal, (5Z)-cyclohexadec-5-en-1-one, 2,6,10-trimethylundec-9-enal, prop-2-enyl hexanoate, (E)-1-(2,6,6-trimethyl-1-cyclohex-2-enyl)but-2-en-1-one, 3-phenylprop-2-en-1-ol, 3,7-dimethylocta-2,6-dienal, 3,7-dimethyloct-6-enyl acetate, [2-(2-methylbutan-2-yl)cyclohexyl] acetate, 3a,4,5,6,7,7a-hexahydro-4,7-methano-1H-inden-5-yl 2-methyl propanoate, 2-pentylcyclopentan-1-ol, (E)-dec-4-enal, 2-pentylcyclopentan-1-one, 2-methoxy-4-propylphenol, methyl 2-hexyl-3-oxocyclopentane-1-carboxylate, phenoxybenzene, ethyl 3-phenylprop-2-enoate, (E)-2-ethyl-4-(2,2,3-trimethyl-1-cyclopent-3-enyl)but-2-en-1-ol, 3-(4-ethylphenyl)-2,2-dimethyl-propanal, 4-methyl-2-(2-methylpropyl)oxan-4-ol, 2-methyldecanenitrile, 5-hexyloxolan-2-one, 5-(diethoxymethyl)-1,3-benzodioxole, 7-hydroxy-3,7-dimethyloctanal, (E)-4-(2,5,6,6-tetramethyl-1-cyclohex-2-enyl)but-3-en-2-one, [(1R,4S,6R)-1,7,7-trimethyl-6-bicyclo[2.2.1]heptanyl] acetate, 6-butan-2-ylquinoline, 2-methoxy-4-prop-1-en-2-ylphenol, (NE)-N-[(6E)-2,4,4,7-tetramethylnona-6,8-dien-3-ylidene]hydroxylamine, (4-propan-2-ylcyclohexyl)-methanol, 2,6-dimethylhept-5-enal, (1R,2S,5R)-5-methyl-2-propan-2-ylcyclohexan-1-ol, ethyl 2-(2-methyl-1,3-dioxolan-2-yl)acetate, 1-phenylethyl acetate, 1-(3,5,5,6,8,8-hexamethyl-6,7-dihydronaphthalen-2-yl)ethanone, 6-butyloxan-2-one, 2,4-dimethyl-2-(5,6,7,8-tetrahydro-5,5,8,8-tetramethyl-2-naphthalenyl)-1,3-dioxolane, (2R,4S)-2-methyl-4-propyl-1,3-oxathiane, 4-(4-hydroxyphenyl)butan-2-one, 3-methyl-5-phenylpentan-1-ol, 4-((1R,5S)-6,6-dimethylbicyclo[3.1.1]hept-2-en-2-yl)-3,3-dimethylbutan-2-one, 3-methylbut-2-enyl acetate, dec-9-en-1-ol, 5-(3-methylphenyl)pentan-1-ol, 3,7-dimethyloctan-3-ol, 1-methoxy-4-[(E)-prop-1-enyl]benzene, 4-hydroxy-3-methoxybenzaldehyde, 9-acetyl-2,6,6,8-tetramethyltricyclo(5.3.1.01,5)undec-8-ene, 2,5-dioxacyclohexa-decane-1,6-dione and mixtures thereof;

b) said hueing agent may comprise a material selected from the group consisting of a small molecule dye, a polymeric dye, a dye clay conjugate, a pigment or mixtures thereof;

c) said brightener may comprise a material selected from the group consisting of disodium 4,4'-bis-(2-sulfostyryl) biphenyl; benzenesulfonic acid, 2,2'-(1,2-ethenediyl)bis[5-[4-[(2-hydroxyethyl)methylamino]-6-(phenylamino)-1,3,5-triazin-2-yl]amino]-, disodium salt; disodium 4,4'-bis{[4-anilino-6-[bis(2-hydroxyethyl)amino-s-triazin-2yl]-amino}-2,2'-stilbenedisulfonate; disodium 4,4'-bis[(4-anilino-6-(N-2-hydroxyethyl-N-methylamino)-s-triazine-2-yl)amino]2,2'-stilbenedisulfonate; disodium 4,4'-bis{[4-anilino-6-methylamino-s-triazin-2-yl]-amino}-2,2'-stilbenedisulfonate; disodium 4,4"-bis[4,6-di-anilino-s-triazin-2-yl]-2,2'-stilbenedisulfonate; disodium 4,4'-bis{[4-anilino-6-morpholino-s-triazin-2-yl]-amino}-2, 2'-stilbenedisulfonate and mixtures thereof;

d) said silicone may comprise a material selected from the group consisting of non-functionalized siloxane polymers, functionalized siloxane polymers, silicone resins, silicone solvents, cyclic silicones and mixtures thereof; and e) said enzyme may comprise a material selected from the group consisting of peroxidases, proteases, lipases, phospholipases, cellobiohydrolases, cellobiose dehydrogenases, esterases, cutinases, pectinases, mannanases, pectate lyases, keratinases, reductases, oxidases, phenoloxidases, lipoxygenases, ligninases, pullulanases, tannases, pentosanases, glucanases, arabinosidases, hyaluronidase, chondroitinase, laccases, amylases, and mixtures thereof.

In one aspect,
a) said small molecule dye may comprise a material selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof;

b) said polymeric dye may comprise polymeric dyes selected from the group consisting of polymers containing conjugated chromogens (dye-polymer conjugates) and polymers with chromogens co-polymerized into the backbone of the polymer and mixtures thereof;

c) said dye clay conjugate may comprise at least one cationic/basic dye and a smectite clay, and mixtures thereof;

d) said non-functionalized siloxane polymer may comprise polydimethylsiloxane, dimethicone, dimethiconol, dimethicone crosspolymer, phenyl trimethicone, alkyl dimethicone, lauryl dimethicone, stearyl dimethicone, phenyl dimethicone, phenylpropyl substituted dimethicone and mixtures thereof.

e) said functionalized siloxane polymer may comprise aminosilicones, amidosilicones, silicone polyethers, silicone-urethane polymers, quaternary ABn silicones, amino ABn silicones, and mixtures thereof.

In one aspect, said hueing agents act to improve the whiteness appearance of dingy white garments or preserve whiteness appearance by compensating for the yellowish appearance of the fabric by addition of a complementary color to the fabric and thus the undesired yellow shade is less noticeable or not noticeable at all. Water soluble blue and violet dyes are commonly used. Suitable hueing dyes include: (a) Small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, such as Direct Violet Colour Index (Society of Dyers and Colourists, Bradford, UK) numbers Direct Violet 9, Direct Violet 35, Direct Violet 48, Direct Violet 51, Direct Violet 66, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Violet 49, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159, Acid Violet 17, Acid Violet 43, Acid Red 73, Acid Red 88, Acid Red 150, Acid Blue 25, Acid Blue 29, Acid Blue 45, Acid Blue 113, Acid Black 1, Direct Blue 1, Direct Blue 71 and Direct Violet 51. (b) Polymeric dyes include polymeric dyes selected from the group consisting of polymers containing conjugated chromogens (dye-polymer conjugates) and polymers with chromogens co-polymerized into the backbone of the polymer and mixtures thereof such as fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® (Milliken, Spartanburg, S.C., USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC and mixtures thereof. (c) Dye clay conjugates include dye clay conjugates selected from the group comprising at least one cationic/basic dye and a smectite clay, and mixtures thereof. (d) Pigments such as Ultramarine Blue (C.I. Pigment Blue 29), Ultramarine Violet (C.I. Pigment Violet 15) and mixtures thereof. In addition, suitable examples of such hueing agents and levels of use are found in U.S. Pat. Nos. 5,770,552, 4,912,203 and U.S. Patent application 2011/0124837 A1 that are incorporated by reference.

Non-limiting brighteners, which also can provide a dye transfer inhibition action, useful in the present invention are those having the general structural formula:

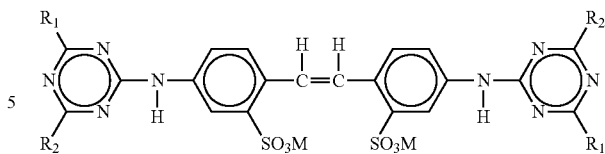

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morphilino, chloro and amino; and NI is a salt-forming cation such as sodium or potassium.

When in the above formula, $R_1$ is anilino, $R_2$ is N-2-bis-hydroxyethyl and M is a cation such as sodium, the brightener is 4,4'-bis[(4-anilino-6-(N-2-bis-hydroxyethyl)-s-triazine-2-yl)amino]-2,2'-stilbenedisulfonic acid and disodium salt. This particular brightener species is commercially marketed under the tradename Tinopal-UNPA-GX® by Ciba Specialty Chemicals Corporation. When in the above formula, $R_1$ is anilino, $R_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]2,2'-stilbenedisulfonic acid disodium salt. This particular brightener species is commercially marketed under the tradename Tinopal 5BM-GX® by Ciba Specialty Chemicals Corporation.

When in the above formula, $R_1$ is anilino, $R_2$ is morphilino and M is a cation such as sodium, the brightener is 4,4'-bis[(4-anilino-6-morphilino-s-triazine-2-yl)amino]2,2'-stilbenedisulfonic acid, sodium salt. This particular brightener species is commercially marketed under the tradename Tinopal AMS-GX® by Ciba Specialty Chemicals Corporation. Some preferred, but non-limiting, brighteners are shown below:

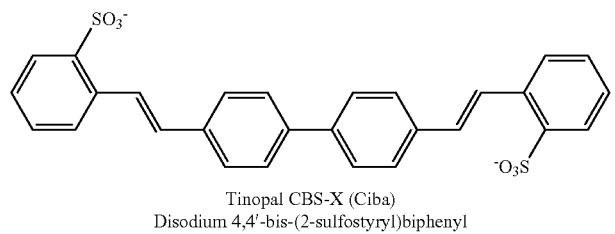

Tinopal CBS-X (Ciba)
Disodium 4,4'-bis-(2-sulfostyryl)biphenyl

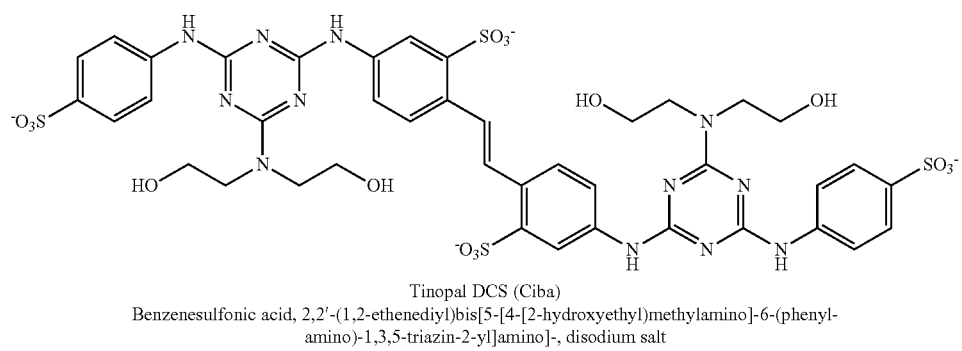

Tinopal DCS (Ciba)
Benzenesulfonic acid, 2,2'-(1,2-ethenediyl)bis[5-[4-[2-hydroxyethyl)methylamino]-6-(phenyl-amino)-1,3,5-triazin-2-yl]amino]-, disodium salt -continued

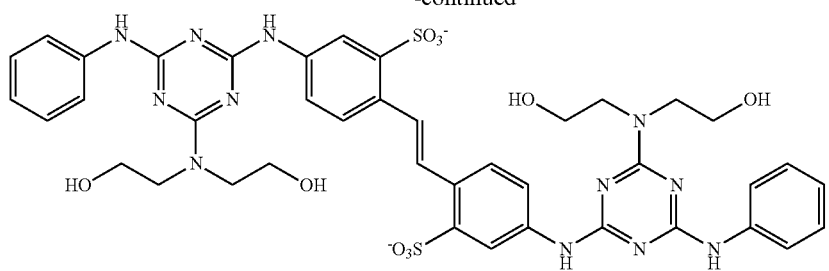

Tinopal UNPA-GX (Ciba)
Disodium 4,4'-bis-{[4-anilino-6-[bis(2-hydroxyethyl)amino-s-triazin-2-yl]-amino}-2,2'-stilbenedisulfonate

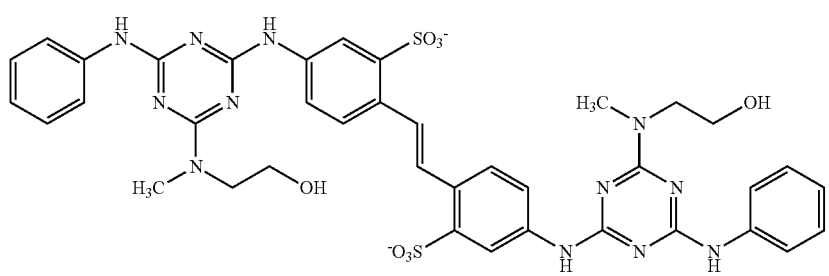

Tinopal 5BM-GX (Ciba)
Disodium 4,4'-bis-[4-anilino-6-(N-2-hydroxyethyl-N-methylamino)-s-triazine-2-yl)amino]-2,2'-stilbenedisulfonate

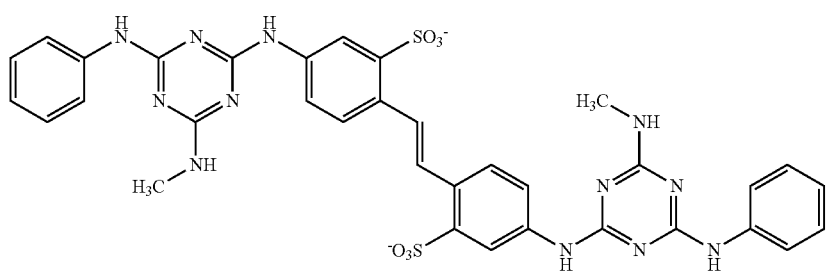

Blankophor HRS (Bayer)
Disodium 4,4'-bis-{[4-anilino-6-methylamino-s-triazin-2-yl]-amino}2,2'-stilbenedisulfonate

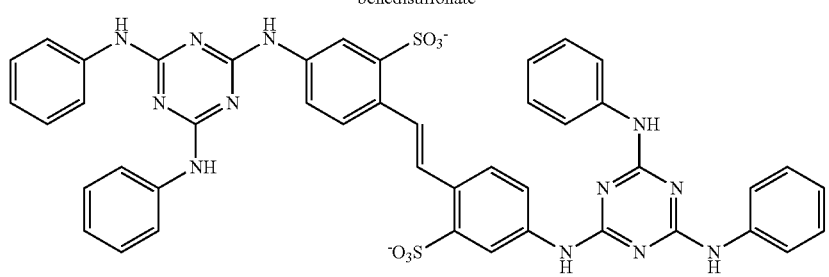

Tinopal TAS (Ciba)
Disodium 4,4''-bis-[4,6-di-anilino-s-triazin-2-yl]-2,2'-stilbenedisulfonate

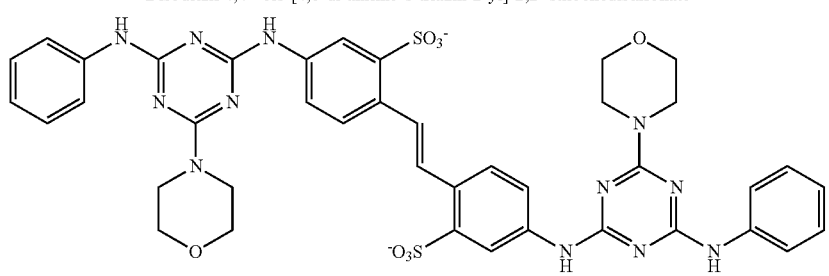

Tinopal AMS-GX (Ciba)
Disodium 4,4'-bis{[4-anilino-6-morpholino-s-triazin-2-yl}-amino}-2,2'-stilbenedisulfonate In one aspect, the Tinopal CBS-X brig especially preferred due to its good stability and performance in laundry.

In one aspect, said silicones may comprise Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may have a viscosity at 25° C. of from about 1 cPs to about 2,000,000 cPs, or from about 5 cPs to about 800,000 cPs, or even from about 10 cPs to 300,000 cPs, or even from about 50 cPs to about 50,000 cPs. In one aspect, suitable organosilicones or mixtures thereof may have a viscosity at 25° C. of from about 10 cPs to about 10,000 cPs, or from about 50 cPs to about 1,000 cPs, or even from about 80 cPs to about 600 cPs.

Silicone materials and silicone resins in particular, might conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence.

Suitable organosilicones may be linear, branched or cross-linked. In one aspect, the organosilicones may comprise a silicone resin. Silicone resins are highly cross-linked polymeric siloxane systems. The cross-linking is introduced through the incorporation of trifunctional and tetrafunctional silanes with monofunctional or difunctional, or both, silanes during manufacture of the silicone resin. As used herein, the nomenclature SiO"n"/2 represents the ratio of oxygen and silicon atoms. For example, $SiO_{1/2}$ means that one oxygen is shared between two Si atoms. Likewise $SiO_{2/2}$ means that two oxygen atoms are shared between two Si atoms and $SiO_{3/2}$ means that three oxygen atoms are shared are shared between two Si atoms.

In one aspect, the organosilicone may comprise polydimethylsiloxane, dimethicone, dimethiconol, dimethicone crosspolymer, phenyl trimethicone, alkyl dimethicone, lauryl dimethicone, stearyl dimethicone, phenyl dimethicone, phenylpropyl substituted dimethicone and mixtures thereof.

In one aspect, the organosilicone may comprise a cyclic silicone. The cyclic silicone may comprise a cyclomethicone of the formula $[(CH_3)_2SiO]_n$ where n is an integer that may range from about 3 to about 7, or from about 5 to about 6.

In one aspect, the organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and mixtures thereof.

Non-limiting examples of suitable silicones are Pulpaid® 3500, Pulpaid® 3600, Xiameter® ACP-0001, Xiameter® PMX-0245 and Xiameter® PMX-0246, Dow Corning® FS1266 from Dow Corning; Silfoam® SD 860, Silfoam® SD 168, Silfoam® SD 850, Silfoam® SD 650, Silfoam® SE 36, Silfoam® SE 39, Silfoam® SC 1092, Silfoam® SC 1132, Silfoam® SC 129, Silfoam® SC 132, Silfoam® SE 47, Silfoam® SRE and Silfoam® SE 90, from Wacker Corp.; Tego 3062 from Goldschmidt; AF-140TG and Tri-Lube-60-PR from Tri-Chem Industries; and Antifoam 2226 from Basildon Chemicals.

In one aspect, said shell may comprise a shell material comprising Polymer 1 and/or Polymer 2 below, said Polymer 1 and Polymer 2 each independently have a weight average molecular weight from about 5,000 Da to about 500,000 Da, from about 10,000 Da to about 300,000 Da, or even from about 20,000 Da to about 240,000 Da:

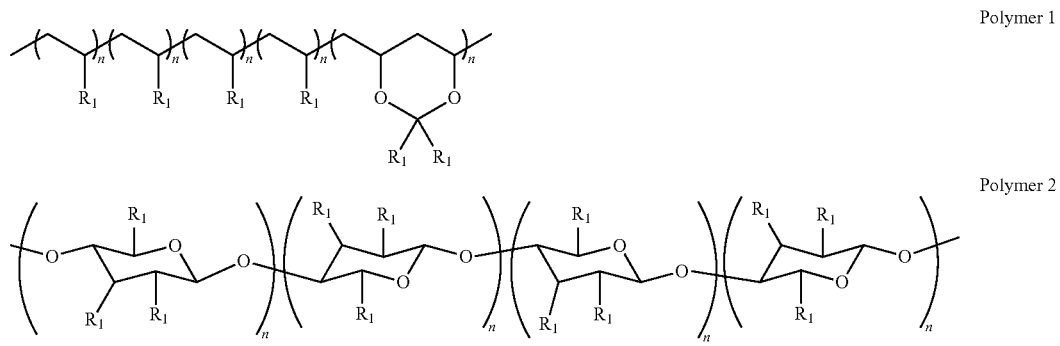

for Polymer 1 and Polymer 2:
each n is independently an integer from 0 to 4,000;
the sum of all integers n in Polymer 1 is an integer from about 60 to about 7,000 and the sum of all integers n in Polymer 2 is an integer from about 60 to about 7,000; and
each $R_1$ in Polymer 1 and Polymer 2 is independently selected from the group consisting of:

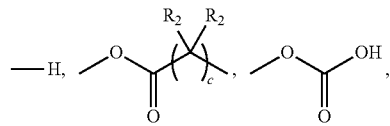

-continued
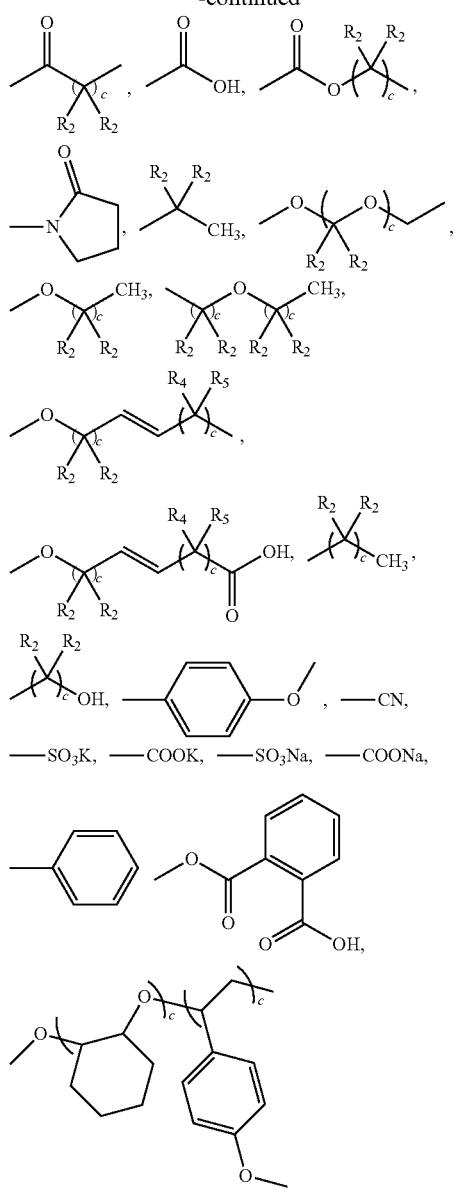
wherein each c is independently an integer from 0 to 60 and each $R_2$ is independently selected from the group consisting of:
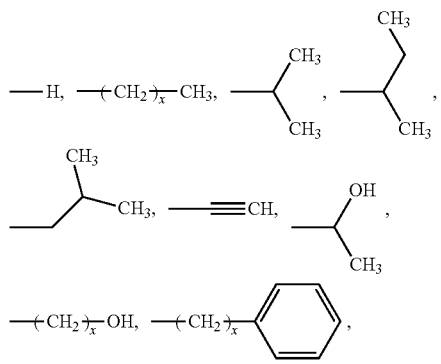
-continued
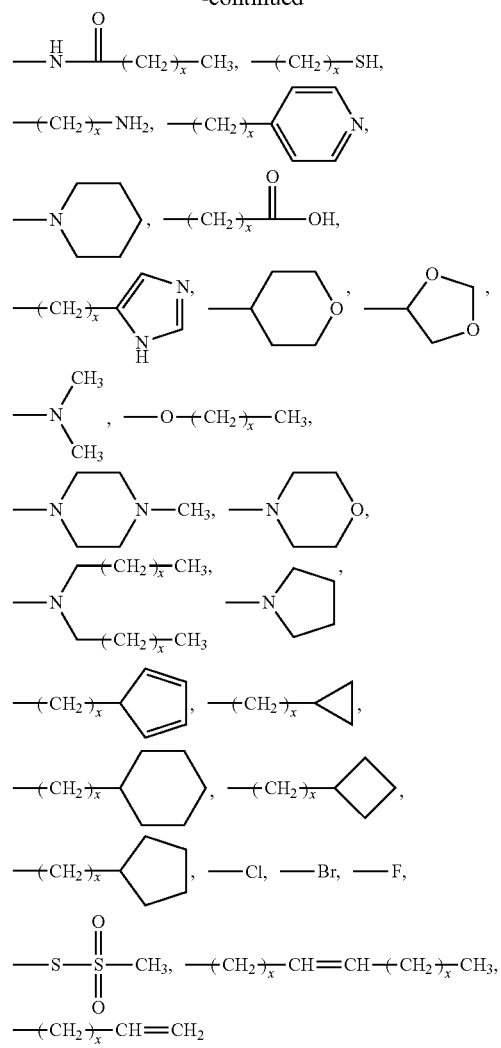
wherein each x is independently an integer from 0 to 60.
In one aspect, each $R_1$, may be independently selected from the group consisting of:
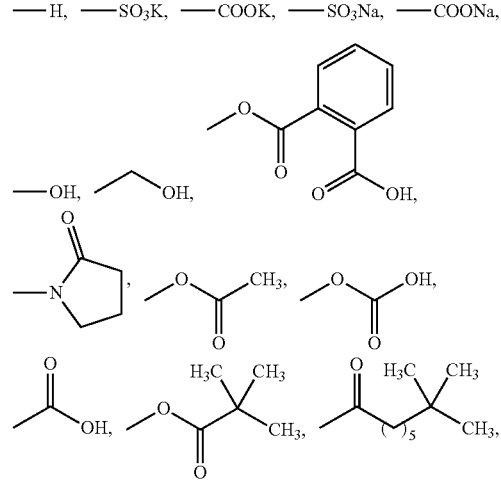

-continued

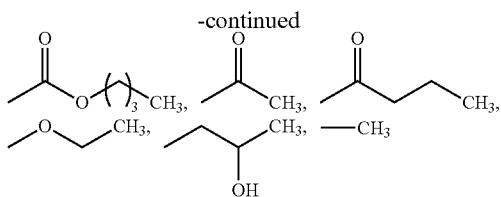

In one aspect, said shell material may comprise, poly (vinyl alcohol), poly(vinyl acetate), poly(vinyl pyrrolidone), poly(vinyl acetate phthalate), vinyl acetate neodecanoic acid co-polymer, vinyl acetate ethylene co-polymer, vinyl acetate crotonic acid neodecanoate co-polymer, vinyl acetate crotonic acid co-polymer, vinyl acetate butyl maleate co-polymer, cellulose acetate, cellulose acetate phthalate, ethyl cellulose, hydroxyl propyl methyl cellulose phathalate, cellulose acetate butyrate, vinyl pyrrolidone vinyl acetate co-polymer, poly(styrene-co-maleic acid) isobutyl ester, poly (styrene-co-butadiene), poly(styrene-co-acrylic) and mixtures thereof.

Non-limiting examples of shell materials may comprise Vinavil® VIN, Vinavil® 6915, Vinavil® 03V, Vinavil EVA® 04 and Vinaflex CR50 from Vinavil S.p.A., Italy; Luviset® CAN, Luviset® CA66 and Luviskol® VA 37 E from BASF, Germany; Sutereric® and Ethocel, Et from Colorcon, U.S.A; Mowiol® grades from Sigma-Aldrich; Antaron-Ganex® V-220 F and Antaron-Ganex® WP-660 from ISP Chemicals, or mixtures thereof.

In one aspect, said core and/or said shell may comprise a viscosity regulator.

In one aspect, said viscosity regulator may comprise a water-soluble solvent, a water-insoluble solvent, silicones, perfume raw materials and/or mixtures thereof, having a viscosity of less than 100 cPs, or less than 80 cPs, or even less than 60 cPs.

Some benefit agents and/or shell material solutions might have a high viscosity pure, after dissolution or dispersion, so certain additives as viscosity regulators might be added to the core and/or the shell as processing aid to facilitate the flow of such benefit agents and/or shell materials through the nozzles. Such viscosity regulators may comprise water-soluble solvents, water-insoluble solvents, perfume raw materials, silicones and/or mixtures thereof. Non-limiting examples include ethanol, propanol, isopropanol, n-propanol, n-butanol, t-butanol, propylene glycol, 1,3-propanediol, ethylene glycol, diethylene glycol, dipropylene glycol, 1,2, 3-propanetriol, propylene carbonate, phenylethyl alcohol, 2-methyl 1,3-propanediol, hexylene glycol, glycerol, sorbitol, polyethylene glycols, 1,2-hexanediol, 1,2-pentanediol, 1,2-butanediol, 1,4 butanediol, 1,4-cyclohexanedimethanol, pinacol, 1,5-hexanediol, 1,6-hexanediol, 2,4-dimethyl-2,4-pentanediol, 2,2,4-trimethyl-1,3-pentanediol (and ethoxylates), 2-ethyl-1,3-hexanediol, phenoxyethanol (and ethoxylates), glycol ethers such as butyl carbitol and dipropylene glycol n-butyl ether, ester solvents such as dimethyl esters of adipic, glutaric, and succinic acids, hydrocarbons such as decane and dodecane, decamethylcyclopentasiloxane, cyclohexasiloxane, ethyl-2-methylbutanoate, ethyl-2-methylbutyrate, isopropyl myristate, ethyl-2-methyl pentanoate, hexyl acetate, allyl caproate and mixtures thereof.

In one aspect, a product comprising the population of encapsulated benefit agents as disclosed herein and an adjunct ingredient is disclosed.

In one aspect, a method of using said product comprising optionally washing rinsing and/or drying a situs, contacting said situs with said product and then optionally washing, rinsing and/or drying said situs is disclosed.

In one aspect, a situs treated with said product is disclosed.

Process of Making Consumer Products

In one aspect of said process of making a consumer product comprising an encapsulated benefit agent and an adjunct material, said process may comprise making an encapsulate by spraying a core composition and a shell solution in a chamber at a temperature of from about 25° C. to about 160° C. by using a concentric flow Focusing® nozzle. In one aspect, said concentric flow focusing nozzle may have an internal diameter from about 100 micrometers to about 500 micrometers, or even from about 250 micrometers to about 400 micrometers. In one aspect, said concentric nozzle may have an external diameter from about 200 micrometers to about 1,000 micrometers, from about 350 micrometers to about 850 micrometers, or even from about 500 micrometers to about 750 micrometers. In one aspect, said encapsulated benefit agent is used as is in a product without further processing said encapsulated benefit agent. In one aspect, said encapsulated benefit agent might be previously agglomerated or dispersed in a liquid before adding it to a consumer product.

In one aspect of said process of making a consumer product comprising an encapsulated benefit agent and an adjunct material, said process may comprise making an emulsion by using a concentric flow Focusing® nozzle and then reacting the shell materials of the emulsion to form covalent bonds such that a core-shell encapsulated benefit agent is produced. In one aspect, the shell material is cross-linked. In one aspect, said concentric flow focusing nozzle may have an internal diameter from about 100 micrometers to about 500 micrometers, or even from about 250 micrometers to about 400 micrometers. In one aspect, said concentric nozzle may have an external diameter from about 200 micrometers to about 1,000 micrometers, from about 350 micrometers to about 850 micrometers, or even from about 500 micrometers to about 750 micrometers. In one aspect, said encapsulated benefit agent is used as is in a product without further processing said encapsulated benefit agent. In one aspect, said encapsulated benefit agent might be previously agglomerated.

In one aspect, the material that is used to make the core portion of said encapsulated benefit agent may have a viscosity from about 0.5 cPs to about 200 cPs, from about 1 cPs to about 100 cPs, or even from about 3 cPs to about 80 cPs.

In one aspect, said shell may comprise a plasticizer. Suitable plasticizers may comprise polyols such as sugars, sugar alcohols, or polyethylene glycols (PEGs), urea, glycol, propylene glycol or other known plasticizers such as triethyl citrate, dibutyl or dimethyl phthalate, polyethylene glycerin, sorbitol, tribuyl citrate, dibutyl sebecate, polysorbates and mixtures thereof.

In one aspect, a binder compatible with the encapsulated benefit agent shell may be used for the agglomeration process of said benefit encapsulated agent. Without being bound by theory, binders may be used to ensure that the particles can be formed with required mechanical strength, provide certain protection avoiding undesired interactions and aid the delivery of the active during the wash cycle. Non-limiting list of suitable binders may include, saccharides and their derivatives, disaccharides such as sucrose, lactose, polysaccharides and their derivatives: starches, cellulose or modified cellulose such as microcrystalline cellulose and cellulose ethers such as hydroxypropyl cellulose (HPC); sugar alcohols such as xylitol, sorbitol or maltitol; proteins such as gelatin; synthetic polymers: polyvinylpyrrolidone (PVP), especially PVP of molecular weight 90,000 Da, polyethylene glycol (PEG), especially those of molecular weight 4,000 Da, 6,000 Da and 9,000 Da, and poly(vinyl alcohol) (PVOH), water impermeable materials from fatty acids, fatty alcohol, fatty esters and waxes or mixtures thereof. In one aspect, the binder is applied in liquid form.

Suitable dispersant agents for the dispersion of said encapsulated benefit agents may comprise a surfactant selected from the group consisting of nonionic, anionic, cationic, ampholytic, zwitterionic, semi-polar nonionic, and mixtures thereof.

Adjunct Ingredients

For the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components supplied by the recited particle. The precise nature of these additional components, and levels of incorporation thereof, will depend on the physical form of the composition and the nature of the operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

Each adjunct ingredient is not essential to Applicants' compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. It is understood that such adjuncts may form a product matrix that is combined with the encapsulates disclosed herein to form a finished consumer product. Generally, when one or more adjuncts are present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Structurants—Non-limiting examples of suitable structurants are:

i. Di-Benzylidene Polyol Acetal Derivative

The fluid detergent composition may comprise from about 0.01% to about 1% by weight of a dibenzylidene polyol acetal derivative (DBPA), or from about 0.05% to about 0.8%, or from about 0.1% to about 0.6%, or even from about 0.3% to about 0.5%. Non-limiting examples of suitable DBPA molecules are disclosed in US 61/167,604. In one aspect, the DBPA derivative may comprise a dibenzylidene sorbitol acetal derivative (DBS). Said DBS derivative may be selected from the group consisting of: 1,3:2,4-dibenzylidene sorbitol; 1,3:2,4-di(p-methylbenzylidene) sorbitol; 1,3:2,4-di(p-chlorobenzylidene) sorbitol; 1,3:2,4-di(2,4-dimethyldibenzylidene) sorbitol; 1,3:2,4-di(p-ethylbenzylidene) sorbitol; and 1,3:2,4-di(3,4-dimethyldibenzylidene) sorbitol or mixtures thereof. These and other suitable DBS derivatives are disclosed in U.S. Pat. No. 6,102,999, column 2 line 43 to column 3 line 65.

ii. Bacterial Cellulose

The fluid detergent composition may also comprise from about 0.005% to about 1% by weight of a bacterial cellulose network. The term "bacterial cellulose" encompasses any type of cellulose produced via fermentation of a bacteria of the genus *Acetobacter* such as CELLULON® by CPKelco U.S. and includes materials referred to popularly as microfibrillated cellulose, reticulated bacterial cellulose, and the like. Some examples of suitable bacterial cellulose can be found in U.S. Pat. Nos. 6,967,027; 5,207,826; 4,487,634; 4,373,702; 4,863,565 and US 2007/0027108. In one aspect, said fibres have cross sectional dimensions of 1.6 nm to 3.2 nm by 5.8 nm to 133 nm. Additionally, the bacterial cellulose fibres have an average microfibre length of at least about 100 nm, or from about 100 to about 1,500 nm. In one aspect, the bacterial cellulose microfibres have an aspect ratio, meaning the average microfibre length divided by the widest cross sectional microfibre width, of from about 100:1 to about 400:1, or even from about 200:1 to about 300:1.

iii. Coated Bacterial Cellulose

In one aspect, the bacterial cellulose is at least partially coated with a polymeric thickener. The at least partially coated bacterial cellulose can be prepared in accordance with the methods disclosed in US 2007/0027108 paragraphs 8 to 19. In one aspect the at least partially coated bacterial cellulose comprises from about 0.1% to about 5%, or even from about 0.5% to about 3%, by weight of bacterial cellulose; and from about 10% to about 90% by weight of the polymeric thickener. Suitable bacterial cellulose may include the bacterial cellulose described above and suitable polymeric thickeners include: carboxymethylcellulose, cationic hydroxymethylcellulose, and mixtures thereof.

iv. Non-Polymeric Crystalline Hydroxyl-Functional Materials

In one aspect, the composition may further comprise from about 0.01 to about 1% by weight of the composition of a non-polymeric crystalline, hydroxyl functional structurant. Said non-polymeric crystalline, hydroxyl functional structurants generally may comprise a crystallizable glyceride which can be pre-emulsified to aid dispersion into the final fluid detergent composition. In one aspect, crystallizable glycerides may include hydrogenated castor oil or "HCO" or derivatives thereof, provided that it is capable of crystallizing in the liquid detergent composition.

v. Polymeric Structuring Agents

Fluid detergent compositions of the present invention may comprise from about 0.01% to about 5% by weight of a naturally derived and/or synthetic polymeric structurant. Examples of naturally derived polymeric structurants of use in the present invention include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. Examples of synthetic polymeric structurants of use in the present invention include: polycarboxylates, polyacrylates, hydrophobically modified ethoxylated urethanes, hydrophobically modified non-ionic polyols and mixtures thereof. In one aspect, said polycarboxylate polymer is a polyacrylate, polymethacrylate or mixtures thereof. In another aspect, the polyacrylate is a copolymer of unsaturated mono- or di-carbonic acid and $C_1$-$C_{30}$ alkyl ester of the (meth)acrylic acid. Said copolymers are available from Noveon inc under the tradename Carbopol Aqua 30.

vi. Di-Amido-Gellants

In one aspect, the external structuring system may comprise a di-amido gellant having a molecular weight from about 150 g/mol to about 1,500 g/mol, or even from about 500 g/mol to about 900 g/mol. Such di-amido gellants may comprise at least two nitrogen atoms, wherein at least two of said nitrogen atoms form amido functional substitution groups. In one aspect, the amido groups are different. In another aspect, the amido functional groups are the same. The di-amido gellant has the following formula:

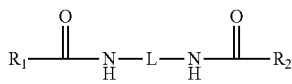

wherein:
$R_1$ and $R_2$ is an amino functional end-group, or even amido functional end-group, in one aspect $R_1$ and $R_2$ may comprise a pH-tuneable group, wherein the pH tuneable amido-gellant may have a pKa of from about 1 to about 30, or even from about 2 to about 10. In one aspect, the pH tuneable group may comprise a pyridine. In one aspect, $R_1$ and $R_2$ may be different. In another aspect, may be the same.

L is a linking moeity of molecular weight from 14 to 500 g/mol. In one aspect, L may comprise a carbon chain comprising between 2 and 20 carbon atoms. In another aspect, L may comprise a pH-tuneable group. In one aspect, the pH tuneable group is a secondary amine In one aspect, at least one of $R_1$, $R_2$ or L may comprise a pH-tuneable group.

Non-limiting examples of di-amido gellants are:
N,N-(2S,2'S)-1,1'-(dodecane-1,12-diylbis(azanediyl))bis(3-methyl-1-oxobutane-2,1-diyl)diisonicotinamide

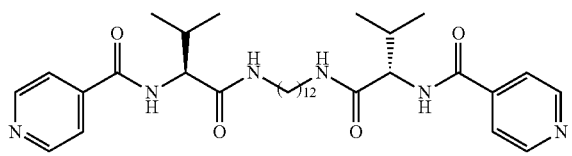

dibenzyl (2S,2'S)-1,1'-(propane-1,3-diylbis(azanediyl))bis(3-methyl-1-oxobutane-2,1-diyl)dicarbamate

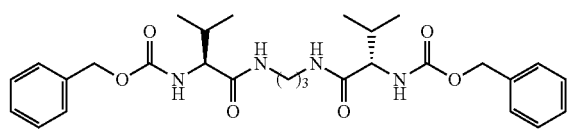

dibenzyl (2S,2'S)-1,1'-(dodecane-1,12-diylbis(azanediyl))bis(1-oxo-3-phenylpropane-2,1-diyl)dicarbamate

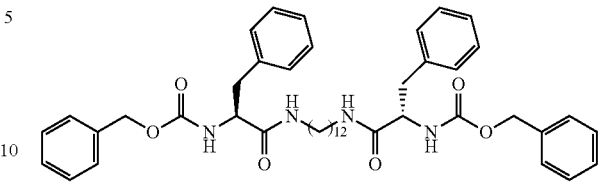

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Perfume Delivery Systems—The compositions of the present invention comprise as another essential ingredient a perfume technology system. Suitable perfume delivery systems, methods of making certain perfume delivery systems and the uses of such perfume delivery systems are disclosed in USPA 2007/0275866 A1. Such perfume delivery systems include:
  I. Polymer Assisted Delivery (PAD): This perfume delivery technology uses polymeric materials to deliver perfume materials. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. PAD includes but is not limited to:

a.) Matrix Systems: The fragrance is dissolved or dispersed in a polymer matrix or particle. Perfumes, for example, may be 1) dispersed into the polymer prior to formulating into the product or 2) added separately from the polymer during or after formulation of the product. Suitable organic latex particles include a wide range of materials including, but not limited to polyacetal, polyacrylate, polyamide, polybutadiene, polychloroprene, polyethylene, polycyclohexylene polycarbonate, polyhydroxyalkanoate, polyketone, polyester, polyetherimide, polyethersulfone, polyethylenechlorinates, polyimide, polyisoprene, polylactic acid, polyphenylene, polyphenylene, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof. All such matrix systems, may include for example polysaccharides and nanolatexes may be combined with other PDTs, including other PAD systems such as PAD reservoir systems in the form of a perfume microcapsule (PMC). Silicone-assisted delivery (SAD) may also be used. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP).

b.) Reservoir Systems: Reservoir systems are also known as a core-shell type technology, or one in which the fragrance is surrounded by a perfume release controlling membrane, which may serve as a protective shell.

II. Molecule-Assisted Delivery (MAD): Non-polymer materials or molecules may also serve to improve the delivery of perfume as perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils.

III. Fiber-Assisted Delivery (FAD): The choice or use of a situs itself may serve to improve the delivery of perfume. In fact, the situs itself may be a perfume delivery technology. For example, different fabric types such as cotton or polyester will have different properties with respect to ability to attract and/or retain and/or release perfume. The amount of perfume deposited on or in fibers may be altered by the choice of fiber, and also by the history or treatment of the fiber, as well as by any fiber coatings or treatments. Fibers may be pre-loaded with a perfume, and then added to a product that may or may not contain free perfume and/or one or more perfume delivery technologies.

IV. Amine Assisted Delivery (AAD): The amine-assisted delivery technology approach utilizes materials that contain an amine group to increase perfume deposition or modify perfume release during product use. There is no requirement in this approach to pre-complex or pre-react the perfume raw material(s) and amine prior to addition to the product. In one aspect, amine-containing AAD materials suitable for use herein may be non-aromatic; for example, polyalkylimine, such as polyethyleneimine (PEI), or polyvinylamine (PVAm), or aromatic, for example, anthranilates. Such materials may also be polymeric or non-polymeric. In one aspect, such materials contain at least one primary amine. In another aspect, a material that contains a heteroatom other than nitrogen, for example sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols.

V. Cyclodextrin Delivery System (CD): This technology approach uses a cyclic oligosaccharide or cyclodextrin to improve the delivery of perfume. Typically a perfume and cyclodextrin (CD) complex is formed. Such complexes may be preformed, formed in-situ, or formed on or in the situs.

VI. Starch Encapsulated Accord (SEA): SEA's are starch encapsulated perfume materials. Suitable starches include modified starches such as hydrolyzed starch, acid thinned starch, starch having hydrophobic groups, such as starch esters of long chain hydrocarbons ($C_5$ or greater), starch acetates, starch octenyl succinate and mixtures thereof. In one aspect, starch esters, such as starch octenyl succinates are employed. Suitable perfumes for encapsulation include the HIA perfumes including those having a boiling point determined at the normal standard pressure of about 760 mmHg at 275° C. or lower, an octanol/water partition coefficient P of about 2,000 or higher and an odour detection threshold of less than or equal 50 parts per billion (ppb). In one aspect, the perfume may have log P of 2 or higher.

VII. Inorganic Carrier Delivery System (ZIC): This technology relates to the use of porous zeolites or other inorganic materials to deliver perfumes. Perfume-loaded zeolite may be used with or without adjunct ingredients used for example to coat the perfume-loaded zeolite (PLZ) to change its perfume release properties during product storage or during use or from the dry situs. Another example of a suitable inorganic carrier includes inorganic tubules, where the perfume or other active material is contained within the lumen of the nano- or micro-tubules. Monomeric and/or polymeric materials, including starch encapsulation, may be used to coat, plug, cap, or otherwise encapsulate the PLT.

VIII. Pro-Perfume (PP): This technology refers to perfume technologies that result from the reaction of perfume materials with other substrates or chemicals to form materials that have a covalent bond between one or more PRMs and one or more carriers. The PRM is converted into a new material called a pro-PRM (i.e., pro-perfume), which then may release the original PRM upon exposure to a trigger such as water or light. Nonlimiting examples of pro-perfumes include Michael adducts (e.g., beta-amino ketones), aromatic or non-aromatic imines (Schiffs Bases), oxazolidines, beta-keto esters, and orthoesters. Another aspect includes compounds comprising one or more beta-oxy or beta-thio carbonyl moieties capable of releasing a PRM, for example, an alpha, beta-unsaturated ketone, aldehyde or carboxylic ester.

a.) Amine Reaction Product (ARP): For purposes of the present application, ARP is a subclass or species of PP. One may also use "reactive" polymeric amines in which the amine functionality is pre-reacted with one or more PRMs, typically PRMs that contain a ketone moiety and/or an aldehyde moiety, to form an amine reaction product (ARP). Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen, for example oxygen, sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, ß-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include manganese, iron and chromium. Suitable MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Inorganic Perhydrate Bleaches—The compositions of detergent components may comprise a hydrogen peroxide source, as an oxygen-releasing bleach. Suitable hydrogen peroxide sources include the inorganic perhydrate salts. Such inorganic perhydrate salts are normally incorporated in the form of the sodium salt at a level of from 1% to 40% by weight, more preferably from 2% to 30% by weight and most preferably from 5% to 25% by weight of the compositions. Non-limiting examples of inorganic perhydrate salts include perborate, percarbonate, perphosphate, persulfate and persilicate salts. The inorganic perhydrate salts are normally the alkali metal salts. The inorganic perhydrate salt may be included as the crystalline solid without additional protection. In one aspect of such granular compositions, inorganic perhydrate salts may comprise a coating which provides better storage stability for the perhydrate salt in the granular product. Sodium perborate can be in the form of the monohydrate of nominal formula $NaBO_2H_2O_2$ or the tetrahydrate $NaBO_2H_2O_2.3H_2O$. Alkali metal percarbonates, particularly sodium percarbonate are preferred perhydrates for inclusion in compositions in accordance with the invention. Sodium percarbonate is an addition compound having a formula corresponding to $2Na_2CO_3.3H_2O_2$, and is available commercially as a crystalline solid. Sodium percarbonate, being a hydrogen peroxide addition compound tends on dissolution to release the hydrogen peroxide quite rapidly which can increase the tendency for localised high bleach concentrations to arise. In one aspect, the percarbonate may be incorporated into such compositions in a coated form which provides in-product stability.

A suitable coating material providing in product stability may comprise a mixed salt of a water soluble alkali metal sulphate and carbonate. Such coatings together with coating processes have previously been described in GB-1,466,799, granted to Interox on 9 Mar. 1977. The weight ratio of the mixed salt coating material to percarbonate lies in the range from about 1:200 to about 1:4, or from about 1:99 to about 1:9, or even from about 1:49 to about 1:19. In one aspect, the mixed salt is of sodium sulphate and sodium carbonate which has the general formula $Na_2SO_4 \cdot n \cdot Na_2CO_3$ wherein n is from about 0.1 to about 3, or from about 0.3 to about 1.0, or even from about 0.2 to about 0.5.

Another suitable coating material providing in product stability, comprises sodium silicate of $SiO_2:Na_2O$ ratio from about 1.8:1 to about 3.0:1, or from about 1.8:1 to about 2.4:1, and/or sodium metasilicate, preferably applied at a level of from about 2% to about 10%, (normally from about 3% to about 5%) of $SiO_2$ by weight of the inorganic perhydrate salt. Magnesium silicate can also be included in the coating. In one aspect, coatings may comprise silicate salts, borate salts, boric acids, other inorganics or mixtures thereof. In one aspect, coatings may comprise waxes, oils, fatty soaps, and mixtures thereof. In one aspect, potassium peroxymonopersulfate may be used.

Peroxyacid Bleach Precursor—Peroxyacid bleach precursors are compounds which react with hydrogen peroxide in a perhydrolysis reaction to produce a peroxyacid. Generally peroxyacid bleach precursors may be represented as

where L is a leaving group and X is essentially any functionality, such that on perhydrolysis the structure of the peroxyacid produced is

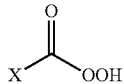

In one aspect, said peroxyacid bleach precursor compounds may be at a level of from about 0.5% to about 20%, or from about 1% to about 10%, or even from about 1.5% to about 5% based on total composition's weight. Suitable peroxyacid bleach precursor compounds may comprise one or more N- or O-acyl groups, which precursors can be selected from a wide range of classes. Suitable classes may include anhydrides, esters, imides, lactams and acylated derivatives of imidazoles and oximes. Non-limiting examples of useful materials within these classes are disclosed in GB-A-1586789. Suitable esters are disclosed in GB-A-836988, 864798, 1147871, 2143231 and EP-A-0170386.

Method of Use

Certain of the consumer products disclosed herein can be used to clean or treat a situs inter alia a surface or fabric. Typically at least a portion of the situs is contacted with an embodiment of Applicants' consumer product, in neat form or diluted in a liquor, for example, a wash liquor and then the situs may be optionally washed and/or rinsed. In one aspect, a situs is optionally washed and/or rinsed, contacted with an aspect of the consumer product and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

Employing one or more of the aforementioned methods results in a treated situs.

Test Methods

It is understood that the test methods that are disclosed in the Test Methods Section of the present application should be used to determine the respective values of the parameters of Applicants' invention as such invention is described and claimed herein. Furthermore, it is obvious to those skilled in the art that encapsulated benefit agents need to be isolated from the product before using the methods below and isolation will depend not only on the type and form of the product but also on the encapsulated benefit agent shell nature. For example, encapsulated benefit agents comprised in a liquid product might be isolated by centrifugation and redisperse in a non-solvent for the encapsulated benefit agent shell, whilst for encapsulated benefit agents comprised in solid products, a solvent for the binder and non-solvent for the encapsulated benefit agent shell might be use.

(1) Mean diameter of a population of encapsulated benefit agents: A population of encapsulated benefit agents is characterized by a mean diameter ($\bar{D}$) obtained using scanning electron microscopy and computerized image analysis with the ImageJ software program version 1.46r (Rasband, W. S., ImageJ, U.S. National Institutes of Health, Bethesda, Md., USA, http://imagej.nih.gov/ij/, 1997-2012.).

i. A sample of a population of encapsulated benefit agents of about 30 mg is adhered to a bioadhesive stub (e.g., 12.5 mm diameter Aluminium Pin Stub G301, mounted with 12 mm diameter Leit Adhesive Carbon tab, as available from Agar Scientific, Essex, UK), avoiding agglomerations to obtain a single, uniform layer of encapsulated benefit agents on the stub.

ii. A Hitachi TM-1000 Table Top Scanning Electron Microscope (Hitachi High-Technologies Europe GmbH, Germany) is used to take about 10 images per stub using a magnification of about 100×, in order to obtain images of about 500 randomly selected encapsulated benefit agents.

iii. From the 10 images taken, at least 3 images are selected for ImageJ analysis, while ensuring that sufficient images are selected to depict a monolayer of at least 300 encapsulated benefit agents, in total.

iv. Each of the 3 or more images is opened in ImageJ. The images are calibrated and the scale used is in micrometers (μm). Each image is converted to 8-bit grayscale pixel depth, and then automatically thresholded by the software's auto threshold button to create a binary image, whereby pixels representing the encapsulated benefit agents become the foreground objects and regions-of-interest, which are separated from the background pixels. The area (in sq·μm) of each region-of-interest object representing an encapsulated benefit agent, is then measured with ImageJ by selecting "Area" on the "Set Measurement" menu, and within "Area" select "Exclude Edge Particles" and "circularity". Then for "circularity" enter the range of values from about 0.4 to about 1 on the "Analyze Particles" menu.

v. The obtained areas (A, in sq·μm) are recorded and used to calculate the diameter of the encapsulated benefit agents according to following formula:

$d_i = \sqrt{(4A_i/\pi)}$ wherein $d_i$ is the diameter in micrometers and A, the area obtained from ImageJ for a given encapsulated benefit agent.

vi. Then, diameters ($d_i$) are rank-ordered from largest to smallest size and the mean encapsulated benefit agent size is obtained using following formula:

$$\overline{D} = \frac{\sum_{i=1}^{n} d_i}{n}$$

wherein $\overline{D}$ is the mean encapsulated benefit agent diameter in micrometers, $d_i$ are the individual diameters of the encapsulated benefit agent as calculated above in micrometers and n the total number of encapsulated benefit agent analyzed, using a minimum of 300 encapsulated benefit agents to obtain such mean. Additionally, the $5^{th}$, $50^{th}$ and $95^{th}$ percentile values are also calculated for these diameter datapoints.

(2) Coefficient of variation of the Diameters of a population of encapsulated benefit agents: A population of encapsulated benefit agents is characterized by a diameter coefficient of variation (CoV) corresponding to the ratio between the diameter distribution of said population of encapsulated benefit agents (ie the standard deviation) and the mean encapsulated benefit agent diameter. CoV is obtained as follow:

i. First, the Standard Deviation (STD) of the mean encapsulated benefit agents' diameter is obtained using following formula:

$$STD = \sqrt{\frac{\sum_{i=1}^{n} (d_i - \overline{D})^2}{n}}$$

wherein STD is the standard deviation of diameters in micrometers, $\overline{D}$ is the mean encapsulated benefit agent diameter in micrometers, $d_i$ are the individual diameters of the encapsulated benefit agents in micrometers as calculated above, and n is the total number
of encapsulated benefit agents analyzed, using a minimum of 300 encapsulated benefit agents to obtain such STD.

ii. Finally, the coefficient of variation (CoV) of the diameters of a population of encapsulated benefit agents is obtained using following formula:

$$CoV = \frac{STD \cdot 100}{\overline{D}}$$

wherein CoV is the coefficient of variation of the diameters of a population of encapsulated benefit agents in %, STD and D are the standard deviation and the mean diameter in micrometers, respectively, as calculated above.

(3) Mean Shell Thickness: The mean shell thickness is determined by preparing cross-sections of targeted encapsulated benefit agents and measuring the shell thickness under a Scanning Electron Microscope (such as model JSM-6400, available from JEOL Ltd, Tokyo, Japan). Approximately 200 mg of encapsulated benefit agent sample (as dry powder) is mixed with about 1 mL of Optimal Cutting Temperature solution (OCT). In the case of non water-soluble shell materials, the OCT solution can be composed of 10.24% poly vinyl alcohol, 4.26% Poly ethylene glycol and 85.5% non-reactive ingredients. Whereas, for water-soluble shell materials, the OCT solution can be comprised of Poly Propylene Glycol, Poly Ethylene Glycol, Glycerin, Vegetable oil and/or Mineral oil. This OCT solution containing the encapsulated benefit agents suspended in it is immediately frozen by using liquid Nitrogen ($-196°$ C.) and is placed inside a cryostat microtome cooled to $-20°$ C. The cryostat microtome is used to cut sample cross-sections of the frozen suspension, at about 10 µm in thickness. Sections are mounted on room temperature glass microscope slides, where they will instantaneously melt and adhere. After the sections are air-dried at room temperature, they are coated with gold by sputter coating and observed and photographed using a scanning electron microscope (SEM) (such as the JEOL SEM model JSM-6400, available from JEOL Ltd, Tokyo, Japan). From the micrographs obtained of the cross-sections, the shell thickness of 30 encapsulated benefit agents is measured, by selecting 10 encapsulated benefit agents in each of 3 different diameter size fractions. The 3 different diameter size fractions are determined by the $5^{th}$, $50^{th}$ and $95^{th}$ percentile values calculated from the diameter datapoints, as measured under method (1) above. The 3 diameter size fractions are defined (in micrometers) as being: the $5^{th}$ percentile value$+/-10\%$ of its value; the $50^{th}$ percentile value$+/-10\%$ of its value; and the $95^{th}$ percentile value$+/-10\%$ of its value. For each of the 30 encapsulated benefit agents selected, the shell thickness is measured at least at 4 different locations spaced equi-distantly around each shell's circumference, i.e., at $0°$, $90°$, $180°$ and $270°$, yielding 120 thickness measurements in total. The mean shell thickness (S) and the standard deviation (STD) of shell thickness of each capsule is calculated using the at least 4 shell thickness measurements for the respective capsule.

(4) Coefficient of variation of the mean shell thickness: the mean shell thickness is characterized by a coefficient of variation (CoVs) corresponding to the ratio between the shell thickness distribution of said population of encapsulated benefit agents (standard deviation) and mean shell thickness of a given encapsulated benefit agent, expressed as a percentage. CoVs is obtained as follow:

i. First, Standard deviation (STDs) of the mean encapsulated benefit agent shell thickness is obtained using following formula:

$$STDs = \sqrt{\frac{\sum_{i=1}^{n} (s_i - \overline{S})^2}{n}}$$

wherein STDs is the standard deviation in micrometers, S is the mean encapsulated benefit agent shell thickness in micrometers, si are the individual shell thickness measurements of the encapsulated benefit agent in micrometers as calculated above and n the total number of shell thickness measurements acquired, using a minimum of 4 measurements to obtain such STD.

ii. Finally, the coefficient of variation (CoVs) of the shell thickness of an encapsulated benefit agent is obtained using following formula:

$$CoVs = \frac{STDs \cdot 100}{\overline{S}}$$

wherein CoVs is the coefficient of variation of a population of encapsulated benefit agents in %, STDs and $\overline{S}$ are the standard deviation and the mean shell thickness in micrometers, respectively, as calculated above.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Examples 1-5: Production of Spray Dried Core-Shell Encapsulates

A polymeric shell material solution is prepared by slowly adding 7.5 grams of poly(vinyl alcohol) (360627, Sigma-Aldrich 80% degree of hydrolysis, Mw 9,000-10,000) to 46.25 grams of deionized water while mixing with a magnetic stirrer at 20° C. Once the poly(vinyl alcohol) is completely dissolved, 46.25 grams of ethanol (≥99%, Sigma-Aldrich) are slowly added under continuous stirring at 20° C. This solution is subsequently filtered with a 5 micrometers Syringe-driven filter (Millex-SV 5.00 μm, Millipore, Ireland). As core, 100 grams of 245 Fluid (99% decamethylcyclopentasiloxane, Dow Corning®) having a viscosity of 4 cPs (measured at a shear rate of 14 $s^{-1}$ and at a temperature of 25° C.) is filtered with a 5 micrometers Syringe-driven filter. The polymeric shell material solution and the core are introduced into the spray dryer (4M8-TriX Spray dryer, ProCepT, Belgium), separately, by using two high pressure syringe pumps (PHD 4400, Harvard Apparatus, France) and using a concentric Flow Focusing® nozzle PSC0350F (Ingeniatrics, Spain). Then, encapsulated benefit agents are collected and the mean diameter (as described in method 1), the coefficient of variation of the mean diameter (as described in method 2), the mean shell thickness (as described in method 3), and the coefficient of variation of the mean shell thickness (as described in method 4). Process parameters and results obtained are summarized in table 1:

Example 6: Production of Spray Dried Core-Shell Encapsulates

A polymeric shell material solution is prepared by slowly adding 7.5 grams of poly(vinyl alcohol) G-Polymer® (Nippon Gohsei, Japan) to 46.25 grams of deionized water while mixing with a magnetic stirrer at 20° C. Once the poly(vinyl alcohol) is completely dissolved, 46.25 grams of ethanol (≥99%, Sigma-Aldrich) are slowly added under continuous stirring at 20° C. This solution is subsequently filtered with a 5 micrometers Syringe-driven filter (Millex-SV 5.00 μm, Millipore, Ireland). As core, 10 grams of poly(vinyl alcohol) (360627, Sigma-Aldrich 80% degree of hydrolysis, Mw 9,000-10,000) are slowly added in 70 grams of deionized water. Once the poly(vinyl alcohol) is dissolved, while stirring, 20 grams of Liquitint Violet DD (Milliken, USA) are slowly added at 20° C. The viscosity of this second solution is measured (as described in method 5) being of 80 cPs. The solutions are introduced into the spray dryer (4M8-TriX Spray dryer, ProCepT, Belgium), separately, by using two high pressure syringe pumps (PHD 4400, Harvard Apparatus, France) and a concentric Flow Focusing® nozzle PSC0350F (Ingeniatrics, Spain). Then, encapsulated benefit agents are collected and further used. The process parameters are:

Internal capillary flow rate (core): 7 ml/h
External capillary flow rate (polymeric shell material): 30 ml/h
Air pressure of the nozzle: 40 mbar
Drying air flow rate: 0.3 $m^3$/min
Drying air temperature: 120° C.

Example 7: Production of Spray Dried Core-Shell Encapsulates

Synthesis of PVA derivative (Bu-PVA): 200 grams Poly (vinyl alcohol) (360627, Mw 9,000-10,000, 80% hydrolyzed, Sigma-Adrich) is added to 800 grams of demineralised water under continuous stirring. The solution is stirred for 5 hours at 20° C. 20 grams of a 37% Hydrochloric acid solution (320331, Sigma-Aldrich) is slowly added to the stirred reaction mixture drop-wise over about 45 minutes. Then, 15 grams butyraldehyde (20710, Sigma-Aldrich) are slowly added to the reaction mixture over about 90 minutes while stirring at 700 rpm. Then, the reaction mixture is stirred for another 18 hours. The reaction flask is neutralised by the addition of 2 M sodium hydroxide aqueous solution and then 500 mL of demineralised water is added. 150 mL portions of the product are each precipitated into 600 mL of fast stirring acetone (179124, Sigma-Aldrich). Each portion

TABLE 1 encapsulated benefit agents examples 1-5

| | Process parameters | | | | | Encapsulated benefit agents characterization | | | |
|---|---|---|---|---|---|---|---|---|---|
| Ex. | Internal capillary flow rate (ml/h) | External capillary flow rate (ml/h) | Air Pressure Nozzle (mbar) | Drying air flow rate ($m^3$/min) | Drying air Temperature (° C.) | Mean diameter (microns) | CoV (%) | Mean Shell Thickness (microns) | CoVs (%) |
| 1 | 3.4 | 26.6 | 100 | 0.3 | 120 | 42.3 | 23.3 | 0.9 | 5.9 |
| 2 | 3.4 | 26.6 | 63 | 0.3 | 100 | 53.8 | 22.4 | 1.1 | 4.6 |
| 3 | 3.4 | 26.6 | 55 | 0.3 | 80 | 32.9 | 22.4 | 1.6 | 5.5 |
| 4 | 10 | 20 | 70 | 0.3 | 100 | 60.6 | 29.9 | 2.4 | 4.2 |
| 5 | 3.4 | 26.6 | 63 | 0.3 | 100 | 39.4 | 20 | 1.9 | 12 | is filtered off, re-dissolved in another 100 mL of demineralised water and then re-precipitated into 600 mL acetone. The combined precipitate is filtered off and washed thoroughly in more acetone. Finally, the product is filtered off and dried overnight to obtain a white semi-amorphous powder with following structure:

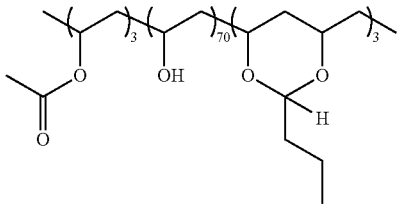

A polymeric shell material solution is prepared by slowly adding 5 grams of synthesized Bu-PVA to 95 grams of demineralized water while mixing with a magnetic stirrer at 20° C. This solution is subsequently filtered with a 5 micrometers Syringe-driven filter (Millex-SV 5.00 μm, Millipore, Ireland). As core, 5 grams of Liquitint® Violet Ion (Milliken, USA) are slowly added to a mixture of 47.5 grams of propylene glycol (>99% purity, INEOS, Germany) and 47.5 grams ethanol (>99% purity, Sigma-Aldrich). The solutions are introduced into the spray dryer (4M8-TriX Spray dryer, ProCepT, Belgium), separately, by using two high pressure syringe pumps (PHD 4400, Harvard Apparatus, France) and using a concentric Flow Focusing® nozzle PSC0350F (Ingeniatrics, Spain). Then, encapsulated benefit agents are collected and further used. The process parameters are:
  Internal capillary flow rate (core): 3 ml/h
  External capillary flow rate (polymeric shell material): 15 ml/h
  Air pressure of the nozzle: 125 mbar
  Drying air flow rate: 0.3 m³/min
  Drying air temperature: 95° C.

Example 8: Production of Spray Dried Core-Shell Encapsulates

A polymeric shell material solution is prepared by slowly adding 2 grams of poly(vinyl acetate) (189480, Sigma-Aldrich) to 98 grams of ethanol (≥99%, Sigma-Aldrich) while mixing with a magnetic stirrer at 20° C. This solution is subsequently filtered with a 5 micrometers Syringe-driven filter (Millex-SV 5.00 μm, Millipore, Ireland). As core, 2 grams of poly(vinyl acetate) (189480, Sigma-Aldrich) are slowly added to 78 grams of ethanol (≥99%, Sigma-Aldrich). Once the poly(vinyl acetate) is dissolved, while stirring, 20 grams of Liquitint® Violet DD (Milliken, USA) are slowly added at 20° C. The viscosity of this second solution is measured (as described in method 5) being of 80 cPs. The solutions are introduced into the spray dryer (4M8-TriX Spray dryer, ProCepT, Belgium), separately, by using two high pressure syringe pumps (PHD 4400, Harvard Apparatus, France) and using a concentric Flow Focusing® nozzle PSC0350F (Ingeniatrics, Spain). Then, encapsulated benefit agents are collected and further used. The process parameters are:
  Internal capillary flow rate (core): 26.6 ml/h
  External capillary flow rate (polymeric shell material): 3.4 ml/h
  Air pressure of the nozzle: 50 mbar
  Drying air flow rate: 0.3 m³/min
  Drying air temperature: 80° C.

Examples 9 and 10: Agglomeration Process for Granular Detergent Composition

|  | Examples | |
|---|---|---|
|  | 9 | 10 |
| $C_{12-15}$ alkyl ethoxylate, with an average of 3 ethoxy groups per molecule | 80 | 75 |
| Polyvinyl Pyrrolidone | 20 | 25 |
| Operating temperature (° C.) | 30 | 30 |
| Viscosity* (cPs) | 900 | 1300 |

*Viscosity is measured at a shear rate of 25 $s^{-1}$ and a temperature of 25° C.

The paste defined in table 1 is sprayed into a Loedige CB mixer (Trade name) at a rate of 1,120 kg/h and at a temperature of 30° C. At the same time zeolite A is added to the mixer at a rate of 1340 kg/h, as well as anhydrous carbonate 1,340 kg/h. Dispersion of the paste premix and high intensity mixing of the premix and the powders occur in the Loedige mixer. The residence time is approximately eight seconds.

The resulting mixture is feed into a Loedige KM mixer (Trade name) and distinct agglomerates are formed. In the second half of the Loedige KM mixer water is sprayed on to the agglomerates at a rate of 225 kg/h promoting the hydration of the carbonate in the agglomerate. After the water spray on, a mixture of zeolite:silica:encapsulated benefit agents (as described in Example 5) in a ration of 30:50:20 is added at a rate of 160 kg/h.

Examples 11, 12 and 13: Liquid Detergent Composition

Non-limiting examples of product formulations containing an encapsulated benefit agent are summarized in the following table

|  | Example 11 | Example 12 | Example 13 |
|---|---|---|---|
| Dosage | 40 ml | 35 ml | 31 ml |
| Ingredients | Weight % | | |
| $C_{11-16}$ alkylbenzene sulfonic acid | 20.0 | 12.5 | 22.0 |
| $C_{12-14}$ alkyl sulfate |  | 2.0 |  |
| $C_{13-14}$ alkyl ethoxy 7-sulfate | 17.0 | 17.0 | 19.0 |
| $C_{13-14}$ alkyl 3-ethoxylate | 7.5 |  | 8.0 |
| Citric acid | 0.9 | 1.0 | 2.0 |
| $C_{13-18}$ Fatty acid | 13.0 | 18.0 | 18.0 |
| Enzymes | 0-3.0 | 0-3.0 | 0-3.0 |
| Ethoxylated Polyethylenimine[1] | 2.2 |  |  |
| Hydroxyethane diphosforic acid | 0.6 | 0.5 | 2.2 |
| Amphiphilic alkoxylated grease cleaning polymer[2] | 2.5 |  | 3.5 |
| Ethylene diamine tetra(methylene phosphonic) acid |  |  | 0.4 |
| Encapsulated benefit agents[3] | 0.2 | 0.3 | 0.3 |
| Perfume microcapsules[4] | 0.4 |  |  |
| Water | 9 | 5 | 10 |
| $CaCl_2$ |  |  | 0.001 |

|  | Example 11 | Example 12 | Example 13 |
|---|---|---|---|
| Perfume | 1.7 | 0.6 | 1.6 |
| Hydrogenated castor oil | 0.4 | 0.3 | 0.3 |
| Minors (antioxidant sufite, aesthetics, etc) | 2.0 | 4.0 | 2.3 |
| Buffers (monoethanolamine) |  | To pH 8.0 |  |
| Solvents (1, 2 propanediol, ethanol) |  | To 100 parts |  |

[1] Polyethyleneimine (Mw: 600 g/mol) with 20 ethoxylane per —NH (BASF, Germany)
[2] PG617 or PG640 (BASF, Germany)
[3] Core-shell encapsulates as described in Example 8.
[4] Perfume microcapsules can be prepared as follows: 25 grams of butyl acrylate-acrylic acid copolymer emulsifier (Colloid C351, 25% solids, pka 4.5-4.7, (Kemira Chemicals, Inc. Kennesaw, Georgia U.S.A.) is dissolved and mixed in 200 grams deionized water. The pH of the solution is adjusted to pH of 4 with sodium hydroxide solution. 8 grams of partially methylated methylol melamine resin (Cymel 385, 80% solids, (Cytec Industries West Paterson, New Jersey, U.S.A.)) is added to the emulsifier solution 200 grams of perfume oil is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylateacrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. 23 grams of acetoacetamide (Sigma-Aldrich, Saint Louis, Missouri, U.S.A.) is added to the suspension.

Examples 14 and 15: Unit Dose Composition

The following are examples of unit dose executions containing an encapsulated benefit agent wherein the composition is enclosed within a PVA film. In one aspect, the film used in the present examples is Monosol M8630 76 μm thickness.

|  | Example 14 | | | Example 15 | | |
|---|---|---|---|---|---|---|
| Compartment | 1 | 2* | 3* | 4 | 5 | 6* |
| Dosage | 34.0 | 3.5 | 3.5 | 25.0 | 1.5 | 4.0 |
| Ingredients | Weight % | | | | | |
| $C_{11-16}$ alkylbenzene sulfonic acid | 20.0 |  |  | 20.0 |  |  |
| $C_{13-14}$ alkyl 7-ethoxylate | 17.0 |  |  | 17.0 |  |  |
| $C_{13-14}$ alkyl ethoxy 3 sulfate | 7.5 |  |  | 7.5 |  |  |
| Citric acid | 2.0 |  |  |  |  |  |
| $C_{13-18}$ Fatty acid | 13.0 |  |  | 18.0 |  |  |
| Enzymes | 0-3.0 |  |  | 0-3.0 |  |  |
| Ethoxylated Polyethylenimine[1] | 2.2 |  |  |  |  |  |
| Hydroxyethane diphosforic acid | 0.6 |  |  |  |  |  |
| Amphiphilic alkoxylated grease cleaning polymer[2] | 2.3 |  |  |  |  |  |
| Ethylene diamine tetra(methylene phosphonic) acid |  |  |  | 0.4 |  |  |
| Encapsulated benefit agent (example 2) |  |  |  |  | 100 |  |
| Encapsulated benefit agent (example 6) |  |  |  |  |  | 100 |
| Encapsulated benefit agent (example 7) |  | 100 | 100 |  |  |  |
| Perfume microcapsules[3] | 0.4 |  |  |  |  |  |
| Water | 9 |  |  | 10.0 |  |  |
| $CaCl_2$ |  |  |  |  |  |  |
| Perfume | 1.7 |  |  | 1.5 |  |  |
| Hydrogenated castor oil | 0.4 |  |  |  |  |  |
| Minors (antioxidant sufite, aesthetics, etc) | 2.0 |  |  | 2.2 |  |  |
| Buffers (monoethanolamine) | To pH 8 | | | | | |
| Solvents (1, 2 propanediol, ethanol) | To 100 parts | | | | | |

[1] Polyethyleneimine (Mw 600 g/mol) with 20 ethoxylane per —NH (BASF, Germany)
[2] PG617 or PG640 (BASF, Germany)
[3] Perfume microcapsules preparation as in Examples 11, 12 and 13.
*No pH adjustment and no solvents are added to these compartments

Examples 16, 17 and 18: Liquid Unit Dose

The following are examples of unit dose executions containing an encapsulated benefit agent wherein the composition is enclosed within a PVA film. The film used in the present examples is Monosol M8630 76 μm thickness, or a water-soluble film according to those disclosed in US Patent Application 2011/0188784A1.

|  | 16 | | | 17 | | 18 | | |
|---|---|---|---|---|---|---|---|---|
|  | 3 compartments | | | 2 compartments | | 3 compartments | | |
| Compartment # | 7 | 8 | 9 | 10 | 11 | 12 | 13 | 14 |
| Dosage (g) | 34.0 | 3.5 | 3.5 | 30.0 | 5.0 | 25.0 | 1.5 | 4.0 |
| Ingredients | Weight % | | | | | | | |
| Alkylbenzene sulfonic acid | 20.0 | 20.0 | 20.0 | 10.0 | 10.0 | 20.0 | 25 | 30 |
| Alkyl sulfate |  |  |  | 2.0 |  |  |  |  |
| $C_{12-14}$ alkyl 7-ethoxylate | 17.0 | 17.0 | 17.0 |  | 7.0 | 17.0 | 15 | 10 |
| $C_{12-14}$ alkyl ethoxy 3 sulfate | 7.5 | 7.5 | 7.5 |  |  | 7.5 | 7.5 |  |
| Citric acid | 0.5 |  | 2.0 | 1.0 |  |  |  | 2.0 |
| Zeolite A |  |  |  | 10.0 |  |  |  |  |
| $C_{12-18}$ Fatty acid | 13.0 | 13.0 | 13.0 |  | 8.0 | 18.0 | 10 | 15 |
| Sodium citrate |  |  |  |  | 4.5 |  |  |  |
| enzymes | 0-3 | 0-3 | 0-3 | 0-3 |  | 0-3 | 0-3 | 0-3 |

-continued

|  | 16<br>3 compartments | | | 17<br>2 compartments | | 18<br>3 compartments | | |
|---|---|---|---|---|---|---|---|---|
| Compartment # | 7 | 8 | 9 | 10 | 11 | 12 | 13 | 14 |
| Dosage (g) | 34.0 | 3.5 | 3.5 | 30.0 | 5.0 | 25.0 | 1.5 | 4.0 |
| Ingredients | | | | Weight % | | | | |
| Sodium Percarbonate | | | | 11.0 | | | | |
| Encapsulated benefit agent from example 8 | 0.5 | | | | 10 | | 50 | |
| Polycarboxylate | | | | 1.0 | | | | |
| Ethoxylated Polyethylenimine[1] | 2.2 | 2.2 | 2.2 | | | | | |
| Hydroxyethane diphosphonic acid | 0.6 | 0.6 | 0.6 | 0.5 | | | 2.2 | |
| Ethylene diamine tetra(methylene phosphonic) acid | | | | | | 0.4 | | |
| Brightener | 0.2 | 0.2 | 0.2 | 0.3 | | 0.3 | | |
| Perfume microcapsules | 0.4 | | | | 5.0 | | | |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, ... ) | 2.0 | 2.0 | 2.0 | 4.0 | 1.5 | 2.2 | 2.2 | 2.0 |
| Buffers (sodium carbonate, monoethanolamine) [2] | | | | To pH 8.0 for liquids<br>To RA > 5.0 for powders | | | | |
| Solvents (1,2 propanediol, ethanol), Sulfate | | | | To 100 p | | | | |

[1] Polyethylenimine (MW 600 g/mol) with 20 ethoxylate groups per —NH.
[2] RA = Reserve Alkalinity (g NaOH/dose)

Example 19: Compositions in Form of Tablets, Especially Tablets for a Laundry or an Automatic Dishwashing Operation

TABLE A

| Binder[1] | A | B | C | D |
|---|---|---|---|---|
| Sorbitol | 2.4 | 2.8 | 1.88 | 2.7 |
| Water | 0 | 0 | 0.12 | 0.25 |
| Glycerin | 0 | 0.4 | 0 | 0.25 |

[1] Values given in table A are percentages by weight of the total detergent tablet.

TABLE B

| Base powder ingredients[2] | E | F |
|---|---|---|
| Anionic/Cationic agglomerates[3] | 35 | 35 |
| Anionic Agglomerates[4] | 1.5 | — |
| Nonionic agglomerates[5] | 12 | 4.50 |
| Clay extrudate[6] | — | 8 |
| Layered Silicate[7] | 1 | 2 |
| Sodium Percarbonate | 10 | 15 |
| Bleach activator agglomerates 1[8] | 4 | — |
| Bleach activator agglomerates 2[9] | — | 3 |
| Sodium Carbonate | 12 | 12 |
| EDDS/Sulphate particle[10] | 0.6 | 0.2 |
| Tetrasodium salt of Hydroxyethane Diphosphonic acid | 0.5 | 0.3 |
| Soil Release Polymer | 6 | 2.5 |
| Encapsualted benefit agent as described in example 6 | 0.1 | 0.1 |
| Zinc Phthalocyanide sulphonate encapsulate[11] | 0.05 | 0.01 |
| Encapsulated benefit agent as described in example 5 | 2 | 1.5 |
| Soap | — | 0.8 |
| Citric acid | 3 | 4 |
| Sodium Citrate | 3 | 2 |
| Sodium Acetate | 4 | 3 |
| Protease | 0.5 | 0.3 |
| Amylase | 0.2 | 0.05 |
| Cellulase | — | 0.1 |
| Perfume | 0.6 | 1 |
| Miscellaneous | to 100% | to 100% |

[2] Values given in table B are percentages by weight of the total detergent tablet.
[3] Anionic/Cationic agglomerates comprise from 20% to 45% anionic surfactant, from 0.5% to 5% cationic surfactant, from 0% to 5% TAE80, from 15% to 30% SKS6, from 10% to 25% Zeolite, from 5% to 15% Carbonate, from 0% to 5% Carbonate, from 0% to 5% Sulphate, from 0% to 5% Silicate and from 0% to 5% Water.
[4] Anionic agglomerates comprise from 40% to 80% anionic surfactant and from 20% to 60% DIBS.
[5] Nonionic agglomerates comprise from 20% to 40% nonionic surfactant, from 0% to 10% polymer, from 30% to 50% Sodium Acetate anhydrous, from 15% to 25% Carbonate and from 5% to 10% zeolite.
[6] Clay agglomerates comprise from 90% to 100% of CSM Quest 5A clay, from 0% to 5% alcohol or diol, and from 0% to 5% water.
[7] Layered silicate comprises from 90% to 100% SKS6 and from 0% to 10% silicate.
[8] Bleach activator agglomerates 1 comprise from 65% to 75% bleach activator, from 10% to 15% anionic surfactant and from 5 to 15% sodium citrate.
[9] Bleach activator agglomerates 2 comprises from 75% to 85% TAED, from 15% to 20% acrylic/maleic copolymer (acid form) and from 0% to 5% water.
[10] Ethylene diamine N,N-disuccinic acid sodium salt/Sulphate particle comprises from 50% to 60% ethylene diamine N,N-disuccinic acid sodium salt, from 20% to 25% sulphate and from 15% to 25% water.
[11] Zinc phthalocyanine sulphonate encapsulates are from 5% to 15% active.

i) Binder A is prepared by heating sorbitol to 105° C. in a 250 ml beaker (Duran® from Schott Glass/Germany) using a laboratory hot plate supplied from IKA Labortechnik.

ii) Base powder E is prepared by mixing the ingredients of base powder E shown in table 2, in a concrete mixing drum (supplied by LESCHA) at atmospheric pressure and ambient temperatures.

iii) 2.4 grams of molten binder A from step i) is sprayed onto 97.6 grams of base powder E from step ii) at a temperature of 105° C. at a pressure of 200 kPa to form a composition.

iv) The composition is allowed to cool down to a temperature of 25° C. and then tableted using a GEPA press. 40 grams of composition is introduced in a 41 by 41 mm square die, and the composition is pressed to obtain detergent tablet having a hardness of 63.74 N as indicated in a VK200 tablet hardness tester (supplied by Van Kell Industries, Inc.).

Examples 20 and 21: Liquid Detergent Composition

Non-limiting examples of product formulations containing an encapsulated benefit agent summarized in the following table

|  | Example 17 | Example 18 |
|---|---|---|
| Dosage | 25 mL | 25 mL |
| Ingredients | Weight % | |
| Monoethanolamine: $C_{12-15}$ EO•3•$SO_3H$ | 37.0 | 35.0 |
| Monoethanolamine: $C_{16-17}$ highly soluble alkyl sulfate | 5.9 | 6.0 |
| $C_{12-14}$ dimethylamine-N-oxide | 1.7 | 1.7 |
| Ethoxylated Polyethyleneimine[1] | 3.9 | 4.0 |
| Citric acid |  | 2.0 |
| Amphiphilic alkoxylated grease cleaning polymer[2] | 3.9 | 2.5 |
| $C_{12-18}$ Fatty acid | 3.0 |  |
| Encapsualted benefit agent as described in example 3 | 0.5 | 0.5 |
| $C_{11-8}$ HLAS | 13.4 | 10.0 |
| HEDP |  | 1.0 |
| Tiron | 2.0 |  |
| Encapsulated benefit agent as described in example 8 | 0.4 |  |
| Perfume microcapsules[3] | 2.3 |  |
| Water | 4.7 | 5.0 |
| Perfume | 1.5 | 1.7 |
| External structuring system | 0.4 | 0.2 |
| Minors (antioxidant, sulfite, aesthetics, . . . ) | 1.5 | 1.5 |
| Buffers (monoethanolamine) | To pH 8.0 | |
| Solvents (1,2 propanediol, ethanol) | To 100 parts | |

[1]Polyethyleneimine (MW 600 g/mol) with 20 ethoxylate groups per —NH (BASF Germany)
[2]PG617 or PG640 (BASF, Germany)
[3]Perfume microcapsules preparation is described in examples 11, 12 and 13.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A population of encapsulated benefit agents having a population diameter coefficient of variation from about 6% to about 50%, said population of encapsulated benefit agents comprising encapsulated benefit agents having a mean diameter of from about 3 micrometers to about 300 micrometers, said encapsulated benefit agent comprising a core and a shell that encapsulates said core, said shell comprising a polymer, said shell having a thickness of from about 0.5 micrometers to about 15 micrometers and a shell thickness coefficient of variation from about 2% to about 30%.

2. A population of encapsulated benefit agents according to claim 1 wherein said shell comprises a film forming polymer.

3. A population of encapsulated benefit agents according to claim 1 having a population diameter coefficient of variation from about 8% to about 35%, said population of encapsulated benefit agents comprising encapsulated benefit agents having a mean diameter of from about 5 micrometers to about 240 micrometers, said encapsulated benefit agent comprising a core and a shell that encapsulates said core, said shell comprising a polymer, said shell having a thickness of from about 1 micrometer to about 8 micrometers, and a shell thickness coefficient of variation from about 4% to about 25%.

4. A population of encapsulated benefit agents according to claim 3 having a population diameter coefficient of variation from about 12% to about 25%, said population of encapsulated benefit agents comprising encapsulated benefit agents having a mean diameter of from about 10 micrometers to about 120 micrometers, said encapsulated benefit agent comprising a core and a shell that encapsulates said core, said shell comprising a polymer, said shell having a thickness of from about 1.5 micrometers to about 6 micrometers and a shell thickness coefficient of variation from about 6% to about 20%.

5. A population of encapsulated benefit agents according to claim 1 wherein said core comprises a material selected from the group consisting of a perfume, a hueing agent, a brightener, a silicone, an enzyme and mixtures thereof.

6. A population of encapsulated benefit agents according to claim 5 wherein:
   a) said perfume comprises a material selected from the group consisting of prop-2-enyl 3-cyclohexylpropanoate, (4aR,5R,7aS,9R)-octahydro-2,2,5,8,8,9a-hexamethyl-4h-4a,9-methanoazuleno(5,6-d)-1,3-dioxole, (3aR,5aS,9aS,9bR)-3a,6,6,9a-tetramethyl-2,4,5,5a,7,8,9,9b-octahydro-1H-benzo[e][1]benzofuran, 4-methoxybenzaldehyde, benzyl 2-hydroxybenzoate, 2-methoxynaphthalene, 3-(4-tert-butylphenyl)propanal, 3a,6,6,9a-tetramethyl-2,4,5,5a,7,8,9,9b-octahydro-1H-benzo[e][1]benzofuran, 3,7-dimethyloct-6-en-1-ol, 3,7-dimethyloct-6-enenitrile, 3-(4-tert-butylphenyl)butanal, 3-(4-propan-2-ylphenyl)butanal, (E)-1-(2,6,6- trimethyl-1-cyclohexa-1,3-dienyl)but-2-en-1-one, decanal, (E)-1-(2,6,6-trimethyl-1-cyclohex-3-enyl)but-2-en-1-one, (5E)-3-methylcyclopentadec-5-en-1-one, 2,6-dimethyloct-7-en-2-ol, ethyl 2-methylpentanoate, ethyl 2-methylbutanoate, 1,3,3-trimethyl-2-oxabicyclo [2,2,2]octane, 2-methoxy-4-prop-2-enylphenol, 3a,4,5,6,7,7a-hexahydro-4,7-methano-1H-indenyl acetate, 3-(3-propan-2-ylphenyl)butanal, a,4,5,6,7,7a-hexahydro-1H-4,7-methanoinden-1-yl propanoate, (2E)-3,7-dimethylocta-2,6-dien-1-ol, (12E)-1-oxacyclohexadec-12-en-2-one, [2-[1-(3,3-dimethylcyclohexyl) ethoxy]-2-methylpropyl]propanoate, hexyl acetate, 2-(phenylmethylidene)octanal, hexyl 2-hydroxybenzoate, (E)-4-(2,6,6-trimethyl-1-cyclohex-2-enyl)but-3-en-2-one, (E)-4-(2,6,6-trimethyl-1-cyclohexenyl)but-3-en-2-one, (E)-3-methyl-4-(2,6,6-trimethyl-1-cyclohex-2-enyl)but-3-en-2-one, 1-(2,3,8,8-tetramethyl-1,3,4,5,6,7-hexahydronaphthalen-2-yl) ethanone, propan-2-yl 2-methylbutanoate, (1R,2S,5R)-5-methyl-2-propan-2-ylcyclohexan-1-ol, (E)-2-ethyl-4-(2,2,3-trimethyl-1-cyclopent-3-enyl)but-2-en-1-ol, 2,4-dimethylcyclohex-3-ene-1-carbaldehyde, 3,7-dimethylocta-1,6-dien-3-ol, 3,7-dimethylocta-1,6-dien-3-yl acetate, 1-((3R,3aS,7R,8aS)-2,3,4,7,8,8a-hexahydro-3,6,8,8-tetramethyl-1H-3a,7-methanoazulen-5-yl)-ethanone, methyl 3-oxo-2-pentylcyclopentaneacetate, 2-methylundecanal, 2-[2-(4-methyl-1-cyclohex-3-enyl)propyl]cyclopentan-1-one, 1-(5,5-dimethyl-1-cyclohexenyl)pent-4-en-1-one, 2-cyclohexylidene-2-phenyl-acetonitrile, 2-phenylethanol, 3,7-dimethyloctan-3-ol, 5-heptyloxolan-2-one, (2-tert-butylcyclohexyl) acetate and mixtures thereof;
b) said hueing agent comprises a material selected from the group consisting of a small molecule dye, a polymeric dye, a dye clay conjugate, a pigment or mixtures thereof;
c) said brightener comprises a material selected from the group consisting of disodium 4,4'-bis-(2-sulfostyryl) biphenyl; benzenesulfonic acid, 2,2'-(1,2-ethenediyl) bis[5-[4-[(2-hydroxyethyl)methylamino]-6-(phenylamino)-1,3,5-triazin-2-yl]amino]-, disodium salt; disodium 4,4'-bis{[4-anilino-6-[bis(2-hydroxyethyl) amino-s-triazin-2yl]-amino}-2,2'-stilbenedisulfonate; disodium 4,4'-bis[(4-anilino-6-(N-2-hydroxyethyl-N-methylamino)-s-triazine-2-yl)amino]2,2'-stilbenedisulfonate; disodium 4,4'-bis{[4-anilino-6-methylamino-s-triazin-2-yl]-amino}-2,2'-stilbenedisulfonate; disodium 4,4"-bis[4,6-di-anilino-s-triazin-2-yl]-2,2'-stilbenedisulfonate; disodium 4,4'-bis{[4-anilino-6-morpholino-s-triazin-2-yl}-amino}-2,2'-stilbenedisulfonate and mixtures thereof;
d) said silicone comprises a material selected from the group consisting of non-functionalized siloxane polymers, functionalized siloxane polymers, silicone resins, silicone solvents, cyclic silicones and mixtures thereof; and
e) said enzyme comprises a material selected from the group consisting of peroxidases, proteases, lipases, phospholipases, cellobiohydrolases, cellobiose dehydrogenases, esterases, cutinases, pectinases, mannanases, pectate lyases, keratinases, reductases, oxidases, phenoloxidases, lipoxygenases, ligninases, pullulanases, tannases, pentosanases, glucanases, arabinosidases, hyaluronidase, chondroitinase, laccases, amylases, and mixtures thereof.

7. A population of encapsulated benefit agents according to claim 6, wherein:
a) said small molecule dye comprises a material selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof;
b) said polymeric dye comprises polymeric dyes selected from the group consisting of polymers containing conjugated chromogens (dye-polymer conjugates) and polymers with chromogens co-polymerized into the backbone of the polymer and mixtures thereof;
c) said dye clay conjugate comprises at least one cationic/basic dye and a smectite clay, and mixtures thereof;
d) said non-functionalized siloxane polymer comprises polydimethylsiloxane, dimethicone, dimethiconol, dimethicone crosspolymer, phenyl trimethicone, alkyl dimethicone, lauryl dimethicone, stearyl dimethicone, phenyl dimethicone, phenylpropyl substituted dimethicone and mixtures thereof;
e) said functionalized siloxane polymer comprises aminosilicones, amidosilicones, silicone polyethers, silicone-urethane polymers, quaternary ABn silicones, amino ABn silicones, and mixtures thereof.

8. A population of encapsulated benefit agents according to claim 1 wherein said shell material comprises, poly(vinyl alcohol), poly(vinyl acetate), poly(vinyl pyrrolidone), poly (vinyl acetate phthalate), vinyl acetate neodecanoic acid co-polymer, vinyl acetate ethylene co-polymer, vinyl acetate crotonic acid neodecanoate co-polymer, vinyl acetate crotonic acid co-polymer, vinyl acetate butyl maleate co-polymer, cellulose acetate, cellulose acetate phthalate, ethyl cellulose, hydroxyl propyl methyl cellulose phathalate, cellulose acetate butyrate, vinyl pyrrolidone vinyl acetate co-polymer, poly(styrene-co-maleic acid) isobutyl ester, poly (styrene-co-butadiene), poly(styrene-co-acrylic) and mixtures thereof.

9. A population of encapsulated benefit agents according to claim 1, wherein said core and/or said shell further comprises a viscosity regulator.

10. A population of encapsulated benefit agents according to claim 9, wherein said viscosity regulator comprises a water-soluble solvent, a water-insoluble solvent, silicones, perfume raw materials and/or mixtures thereof, having a viscosity of less than about 100 cPs.

11. A product comprising the population of encapsulated benefit agents selected from those of claim 1 and an adjunct ingredient.

12. A method of using the product of claim 11 comprising the steps of optionally washing rinsing and/or drying a situs, contacting said situs with the product of claim 11 and then optionally washing rinsing and/or drying said situs.

13. A situs treated with a product according to claim 12.

* * * * *